United States Patent [19]

Jikihara et al.

[11] Patent Number: 5,672,566

[45] Date of Patent: Sep. 30, 1997

[54] SYNERGISTIC HERBICIDAL COMPOSITIONS COMPRISING 1,3-OXAZIN-4-ONE COMPOUNDS

[75] Inventors: Kazuo Jikihara; Hisato Suzuki, both of Ami-machi; Yumiko Miyashita, Tsukigata-machi; Toshishiro Maruyama, Ami-machi; Yoshihiro Usui, Ami-machi; Futaba Makimura, Ami-machi; Jiro Morishige, Ami-machi, all of Japan

[73] Assignee: Rhone-Poulenc Agrochimie, Lyons, France

[21] Appl. No.: 583,073

[22] PCT Filed: Jul. 12, 1994

[86] PCT No.: PCT/JP94/01133

§ 371 Date: Feb. 5, 1996

§ 102(e) Date: Feb. 5, 1996

[87] PCT Pub. No.: WO95/02329

PCT Pub. Date: Jan. 26, 1995

[30] Foreign Application Priority Data

| Jul. 13, 1993 | [JP] | Japan | 5-195260 |
| Jul. 13, 1993 | [JP] | Japan | 5-195272 |

[51] Int. Cl.⁶ ................................ A01N 43/86
[52] U.S. Cl. ................................ 504/130
[58] Field of Search ................. 504/130, 223; A01N 43/86

[56] References Cited

U.S. PATENT DOCUMENTS 5,436,224  7/1995  Hamatani et al. ............ 504/223

FOREIGN PATENT DOCUMENTS

| 5-201811 | 8/1993 | Japan . |
| WO93/15064 | 8/1993 | WIPO . |

*Primary Examiner*—S. Mark Clardy
*Attorney, Agent, or Firm*—Wenderoth, Lind & Ponack

[57] ABSTRACT

A herbicidal composition containing as active ingredients the following two components, (A): at least one of 1,3-oxazin-4-one derivatives represented by the following general formula (I)

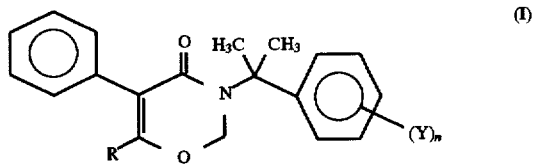

wherein, R is a methyl or an ethyl group, Y is a halogen atom, a lower haloalkyl or a lower haloalkoxy group, and n is 0, 1, 2 or 3, and (B): at least one compound selected from certain known herbicides. It is possible, by use of this composition, to completely control annual gramineous weeds, annual broad-leaved weeds and perennial weeds, without causing any phytotoxicity on agriculturally important crops at a low dose of the active ingredients.

23 Claims, No Drawings

SYNERGISTIC HERBICIDAL COMPOSITIONS COMPRISING 1,3-OXAZIN-4-ONE COMPOUNDS

This application has been filed under 35USC 371 from International application PCT/JP94/01133 filed Jul. 12, 1994.

TECHNICAL FIELD

This invention relates to a herbicidal composition, and more detailedly relates to a herbicidal composition which contains as active ingredients a mixture of a certain 1,3-oxazin-4-one derivative and one or more certain known herbicides, and has a broad weed-control spectrum and can exert a sufficient herbicidal effect at a low dose of the active ingredients.

BACKGROUND ART

Many herbicides have so far been put to practical use in paddy fields, and they have generally widely been used as a single active ingredient preparation or a mixture containing two or more of active ingredients. However, although these agents are comparatively effective for annual weeds, they are less effective for perennial weeds, and thus it is the present state of things that perennial weeds having strong reproductivity such as Scirpus juncoides (Common name: Japanse bulrush), Sagittaria pygmaea (Japanese common name: Urikawa) and Cyperus serotenus (Japanese common name: Mizugayatsuri) tend to increase in paddy fields in Japan in recent years, and it is strongly desired to develop herbicides also effective for these perennial weeds.

The present inventors have intensely studied for developing herbicides satisfying the above requirements, and now found such herbicidal composition by combining the certain novel 1,3-oxazin-4-one derivative which the present inventors previously developed and proposed (see International Publication No. WO 93/15064) with certain known herbicides having different weed-control mechanisms and weed-control spectra. In this invention a wide range of weeds in paddy fields can selectively be controlled, moreover the herbicidal effect is synergistically increased compared with the case in which they are used alone respectively. Consequently this invention has made it applicable at a low dose of active ingredients, and furthermore the weed-control spectrum enlarged. Thus this invention has been completed.

DISCLOSURE OF INVENTION

The herbicidal composition of this invention is consisted of the following two components A and B.

Component A
at least one derivative selected from the 1,3-oxazin-4-one derivatives represented by the following general formula (I)

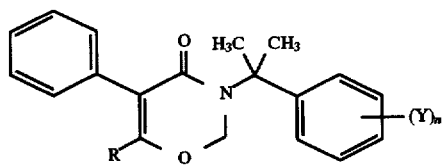

(I)

wherein, R is a methyl or an ethyl group, Y is a halogen atom, a lower haloalkyl or a lower haloalkoxy group, and n is 0, 1, 2 or 3, and Component B
at least one compound selected from 5-tert-butyl-3-(2,4-dichloro-5-isopropoxyphenyl)-1,3,4-oxadiazol-2-(3H)one, 1,3-dimethyl-4-(2,4-dichloro-3-methylbenzoyl)-5-(4-methyl-phenacyloxy)pyrazole, 2-(2,4-dichloro-m-tolyloxy)propionanilide, (RS)-2-bromo-3,3-dimethyl-N-(1-methyl-1-phenylethyl)-3,3-dimethylbutylamide, 2,3-dihydro-3,3-dimethylbenzofuran-5-yl ethanesulfonate, 1-(α,α-dimethylbenzyl)-3-p-tolylurea, 1-(2-chlorobenzyl)-3-(α,α-dimethylbenzyl)urea, 4'-nitrophenyl-2,4,6-trichlorophenyl ether, methyl 5-(2,4-dichlorophenoxy)-2-nitrobenzoate, 2,4-bis(ethylamino)-6-methylthio-S-triazine and 2-(1,2-dimethylpropylamino)-4-ethylamino-6-methylthio-1,3,5-triazine, N'-(2-chloroimidazol[1,2,-a]pyridin-3-yl-sulfonyl)-N'-(4,6-dimethoxy-2-pyrimidyl)urea, methyl 2-[[[[(4,6-dimethoxy-2-pyrimidinyl)-amino]carbonyl]amino]sulfonyl]methyl]benzoate, ethyl 5-(4,6-dimethoxypyrimidin-2-yl-carbamoylsulfamoyl)-1-methylpyrazole-4-carboxylate, and 5-[(4,6-dimethoxypyrimidin-2-yl)aminocarbonylaminosulfonyl]-1-methyl-4-(2-methyl-1,2,3,4-tetrazol-5-yl)-pyrazole.

The herbicidal composition of the present invention is further detailedly described below.

1,3-Oxazin-4-one derivatives represented by the above general formula (I) used as component A in the herbicidal composition of the present invention are novel compounds not disclosed in prior publications, and details of preparation process, physical properties, herbicidal activities thereof are disclosed in the specification of International Publication No. WO 93/15064.

The term "lower" in the present specification means that a group or compound to which this term is attached has 6 or less carbon atoms.

In the compounds of the above formula (I), the "halogen atom" represented by Y includes fluorine, chlorine, bromine and iodine atoms; the "lower haloalkyl group" is a lower haloalkyl group of which at least one of the hydrogens is replaced with a halogen atom. This includes, for example, bromomethyl, dichloromethyl, trifluoromethyl, 2-iodoethyl, 1-chloroethyl, 3-chloropropyl, 2-methyl-2-chloropropyl and 2,2,2-trifluoroethyl groups, etc., and the "lower haloalkoxy group" is a lower haloalalkoxy group of which at least one of the hydrogen atoms is replaced with a halogen atom, and includes, for example, trifluoromethoxy, difluoromethoxy, chlorodifluoromethoxy, 2-chloroethoxy, 1,1,2,2-tetrafluroethoxy, 3-chloropropoxy and 2,2,3,3,3-pentafluoropropoxy groups, etc.

Representative examples of the compounds of the formula (I) are as follows.

No. 1: 6-methyl-3-[1-methyl-1-(3,5-dichlorophenyl)ethyl]-5-phenyl-2,3-dihydro-4H-1,3-oxazin-4-one No. 2: 6-methyl-3-[1-methyl-1-(1-chlorophenyl)ethyl]-5-phenyl-2,3-dihydro-4H-1,3-oxazin-4-one No. 3: 6-methyl-3-[1-methyl-1-(3-fluorophenyl)ethyl]-5-phenyl-2,3-dihydro-4H-1,3-oxazin-4-one No. 4: 6-methyl-3-[1-methyl-1-(4-fluorophenyl)ethyl]-5-phenyl-2,3-dihydro-4H-1,3-oxazin-4-one No. 5: 6-methyl-3-[1-methyl-1-(2-chlorophenyl)ethyl]-5-phenyl-2,3-dihydro-4H-1,3-oxazin-4-one No. 6: 6-methyl-3-[1-ethyl-1-(3-methylphenyl)ethyl]-5-phenyl-2,3-dihydro-4H-1,3-oxazin-4-one No. 7: 6-methyl-3-[1-methyl-1-(3-difluoromethoxyphenyl)ethyl]-5-phenyl-2,3-dihydro-4H-1,3-oxazin-4-one Compounds represented by the above formula (I) can, for example, be prepared by the process shown in the following reaction formula:

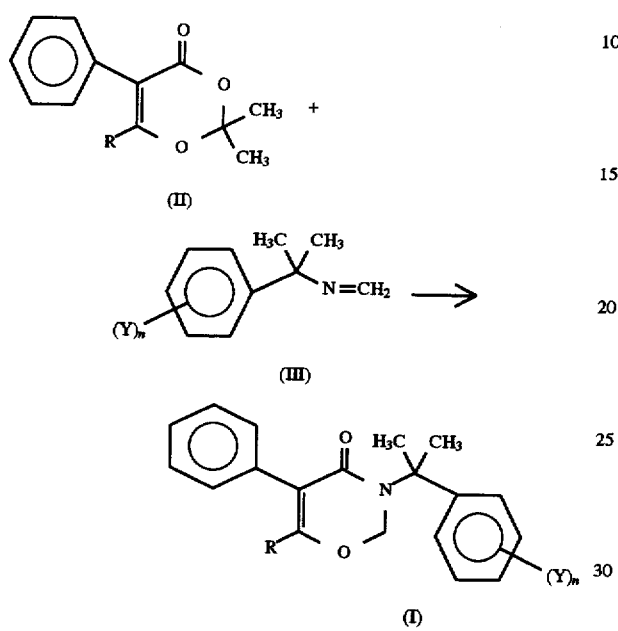

wherein, R, Y and n are as defined above.

The reaction of a compound of the above formula (II) with a compound of the above formula (III) can be performed in a suitable solvent or without any solvent, and the reaction temperature can usually be a temperature between about 90° C. and about 160° C. or the boiling point of the solvent used. As to the solvent when used, there is no particular limitation so long as it is substantially inert to the above reaction, but it is preferable, from the viewpoint of the above reaction temperature, to use an organic solvent of high boiling point such as toluene, xylene or mesitylene, which has a boiling point over 90° C. The reaction time varies depending on other reaction conditions to be used, but the reaction can generally be completed in 1 to 120 minutes.

The use ratio of the compound of the formula (III) to the compound of the formula (II) is not strictly limited, either, but it is usually suitable to use the compound of the formula (III) within the range of 0.5 to 2 moles, particularly 0.9 to 1.1 moles per mole of the compound of the formula (II).

The compound of the formula (I) formed can be separated and purified according to a process known per se, such as, for example, recrystallization, extraction or chromatography.

Compounds of the formula (II) used as a starting material in the above reaction can be prepared according to a process known per se, for example the process disclosed in Chem. Pharm. Bull., 31 (6), 1895–1901 (1983), and compounds of the formula (III) can also be prepared according to a process known per se, for example the process disclosed in U.S. Pat. No. 2,571,759.

More specifically, a compound of the formula (III) can, for example, be prepared, according to the following reaction formula, by adding a compound of the formula (V) dropwise to formalin

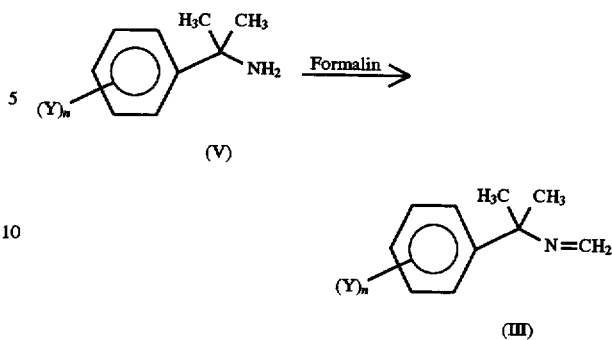

wherein, Y is as defined above.

The reaction temperature is desirably selected as room temperature. The reaction time varies depending other reaction conditions, but the reaction can usually be completed within 0.1 to 10 hours. The compound of the formula (III) can be separated from the reaction mixture by a conventional method, and readily purified by recrystallization, distillation, column chromatography, or the like.

On the other hand, the compounds of (1) to (15) to be used as the component B of the herbicidal composition of the present invention are herbicides known per se and usually used, and their details are disclosed, for example in the following publications.

(1) 5-tert-butyl-3-(2,4-dichloro-5-isopropoxyphenyl)-1,3,4-oxadiazol-2-(3H)one

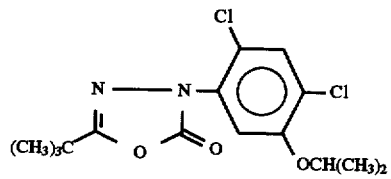

see Japanese Patent Publication No. 15649/1969 (hereafter this compound is referred to as "G-315")

(2) 1,3-dimethyl-4-(2,4-dichloro-3-methyl-benzyol)-5-(4-methyl-phenacyloxy)pyrazole

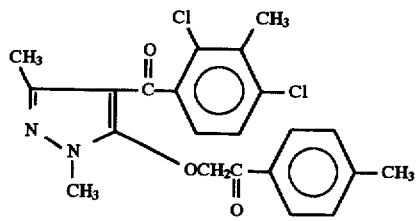

see Japanese Laid-Open Patent Publication No. 19402/1987 (hereinafter this compound is referred to as "MY-71")

(3) 2-(2,4-dichloro-5-m-tolyloxy)-propionanilide

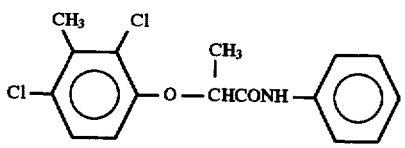

see Japanese Laid-Open Patent Publication No. 171904/1982 (hereinafter this compound is referred to as "MY-15")

(4) 2-bromo-3,3-dimethyl-N-(1-methyl-1-phenylethyl) butylamide

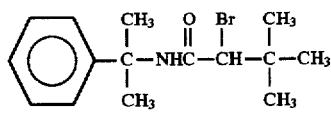

see U.S. Pat. No. 4,288,244 (hereinafter this compound is referred to as "S-47")

(5) 2,3-dihydro-3,3-dimethylbenzofuran-5-yl ethanesulfonate

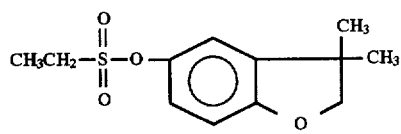

see Japanese Patent Publication No. 45523/1980 (hereinafter this compound is referred to as "NS-112")

(6) 1-(α,α-dimethylbenzyl)-3-p-tolylurea

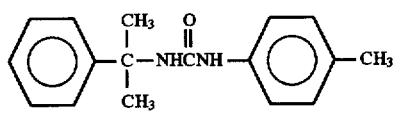

see Japanese Patent Publication No. 35454/1973 (hereinafter this compound is referred to as "SK-23")

(7) 1-(2-chlorobenzyl)-3-(α,α-dimethylbenzyl)-urea

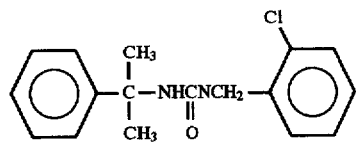

see Japanese Laid-Open Patent Publication No. 172910/1985 (hereinafter this compound is referred to as "JC-940")

(8) 4'-nitrophenyl-2,4,6-trichlorophenyl ether

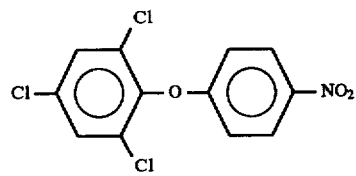

see U.K. Patent No.1,016,648 (hereinafter this compound is referred to as "CNP")

(9) methyl 5-(2,4-dichlorophenoxy)-2-nitrobenzoate

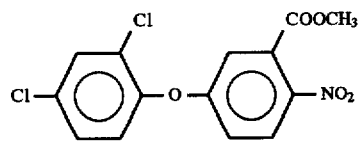

see Japanese Patent Publication No. 4609/1973 (hereinafter this compound is referred to as "MC-79")

(10) 2,4-bis(ethylamino)-6-methylthio-S-triazine

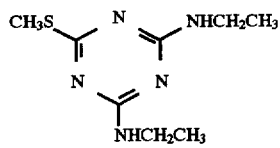

see Swiss Patent No. 337,019 (hereinafter this compound is referred to as "G 32911")

(11) 2-(1,2-dimethylpropylamino)-4-ethylamino-6-methylthio-1,3,5-triazine

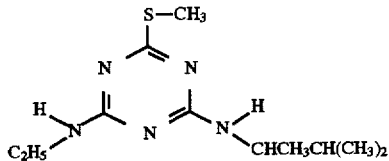

see Belgian patent No. 714,992 (hereinafter this compound is referred to as "CG-7013")

(12) N'-(2-chloroimidazolyl[1,2-a]pyridin-3-yl-sulfonyl)-N'-(4,6-dimethoxy-2-pyrimidyl)urea

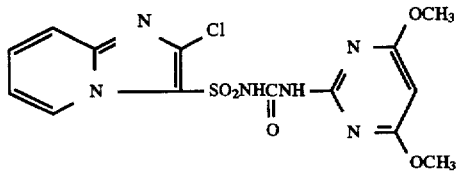

see Japanese Laid-Open Patent Publication No. 139582/1989 (hereinafter this compound is referred to as "TH-913")

(13) methyl 2-[[[[[(4,6-dimethoxy-2-pyrimidinyl)amino] carbonyl]amino]sulfonyl]methyl]-benzoate

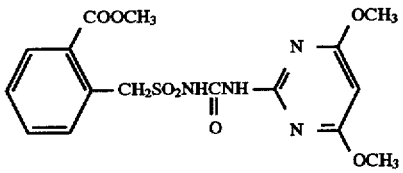

see Japanese Patent Publication No. 112379/1982 (hereinafter this compound is referred to as "DPX-84")

(14) ethyl 5-(4,6-dimethoxypyrimidin-2-yl-carbamoylsulfamoyl)-1-methylpyrazole-4-carboxylate

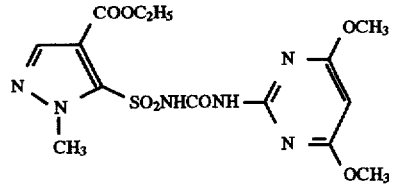

see Japanese Laid-Open Patent Publication No. 122488/1984 (hereinafter this compound is referred to as "NC-311")

(15) 5-[(4,6-dimethoxypyrimidin-2-yl) aminocarbonylaminosulfonyl]-1-methyl-4-(2-methyl- 1,2,3,4-tetrazol-5-yl)-pyrazole

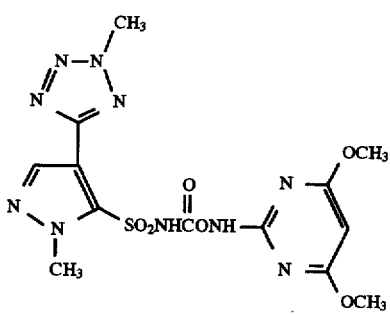

see Japanese Laid-Open Patent Publication No. 41007/1991 (hereinafter this compound is referred to as "DPX-47")

Still another herbicide can also be cited as a mixing component for the herbicidal composition of the present invention for the purpose of enhancement of its herbicidal activity, enlargement of the spectrum of weeds to be targeted, enlargement of suitable time length for treatment, enlargement of residual efficacy, reduction of phytotoxicity under bad conditions or the like. The following compounds can, for example, be mentioned as other herbicides for this invention.

Phenoxy group 2,4-dichlorophenoxyacetic acid (common name: 2,4-D, see THE PESTICIDE MANUAL 9th edd., (1991), p218–219), 4-(4-chloro-3-methylphenoxy)butyric acid (common name: MCPB, see U.K. Patent No. 758,980), 4-chloro-2-methylphenoxyacetic acid (common name: MCPA, see THE PESTICIDE MANUAL 9th edd., (1991), P533), 2-(2-naphthyloxy)propionanilide (common name: Naproanilide, see THE PESTICIDE MANUAL 9th edd., (1991), p610), S-ethyl (4-chloro-2-methylphenoxy)ethanethioate (common name: MCPA-thioethyl, see U.S. Pat. No. 3,708,278), etc.

Diphenyl ether group 2,4-dichlorophenyl 3'-methoxy-4'-nitro-phenyl ether (common name: Chlomethoxynyl, see Pesticides Handbook, 1989 edd., p500)

Acid amide group

N-butoxymethyl-2-chloro-2'6'-diethylacetanilide (common name: Butachlor, see U.S. Pat. No. 3,442,945), 2-chloro-2',6'-diethyl-N-(n-propoxyethyl)acetanilide (common name: Prethylachlor, see Japanese Laid-Open Patent Publication No. 54527/1974), 2-benzothiazol-2-yloxy-N-methyl-acetanilide (common name: Mefenacet, see Japanese Laid-Open Patent Publication No. 154762/1979), etc.

Diazine group 4-(2,4-dichlorobenzoyl)-1,3-dimethylpyrazol-5-yl toluene-4-sulfonate (common name: Pyrazolate, see Japanese Laid-Open Patent Publication No. 126830/1975).

2-[[4-(2,4-dichlorobenzoyl)-1,3-dimethyl-1H-pyrazol-5-yl]oxy]-1-phenylethanone (common name: Pyrazoxyphenone, see U.K. Patent No. 2,002,375), 3-isopropyl-1H-2,1,3-benzothiadiazin-4(3H)-one-2,2-dioxide (common name: Benthazone, see U.S. Pat. No. 3,708,277)

Carbamate group

S-1-methyl-1-phenylethyl piperidine-1-carbothioate (common name: Dimepiperate, Japanese Laid-Open Patent Publication No. 98331/1976), methyl (3,4-dichlorophenyl)-carbamate (common name: Swep, see THE PESTICIDE MANUAL 9th edd., (1991), P927), S-(4-chlorobenzyl)-diethyl-thiocarbamate (common name: Thiobencarb, see Japanese Patent Publication No. 29024/1968), S-ethyl hexahydro-1H-azepine-1-carbothioate (common name: Morinate, see U.S. Pat. No. 3,198,786)

S-benzyl-1,2-diethylpropyl(ethyl)thiocarbamate (common name: Esprocarb, see U.S. Pat. No. 3,742,005), etc.

Organophosphorus group

S-2-methylpiperidinocarbonylmethyl O,O-dipropylphosphorodithioate (common name: Piperophos, see Belgian Patent No. 725,992), S-2-benzensulfonylaminoethyl O,O-diisopropylphosphorothioate, etc.

The above-mentioned herbicides can be mixed additionally when needed, and these are referred to as "component C".

An insecticide, a fungicide, a plant growth regulator, etc. can, if necessary, be added to the herbicidal composition of the present invention.

There is no particular limitation about combination of the 1,3-oxazin-4-one derivatives represented by the above formula (I) (components A) with the compounds of the above (1) to (15) (components B) in the herbicidal composition of the present invention, but the following combinations can be mentioned as preferred ones.

Component A: compound No. 1 with component B: G-315,

Component A: compound No. 1 with component B: MY-71,

Component A: compound No. 1 with component B: SK-23,

Component A: compound No. 1 with component B: CNP,

Component A: compound No. 1 with component B: MC-79,

Component A: compound No. 1 with components B: MY-71 and S-47,

Component A: compound No. 1 with components B: MY-71 and JC-940,

Component A: compound No. 1 with components B: MY-71, MY-15 and S-47,

Component A: compound No. 1 with components B: MY-71, MY-15 and NS-112,

Component A: compound No. 1 with component B: G32911,

Component A: compound No. 1 with component B: TH-913,

Component A: compound No. 1 with components B: TH-913 and SK-23,

Component A: compound No. 1 with component B: DPX-84,

Component A: compound No. 1 with components B: DPX-84 and SK-23,

Component A: compound No. 1 with component B: NC-311,

Component A: compound No. 1 with components B: NC-311 and SK-23,

Component A: compound No. 1 with components B: DPX-84 and DPX-47,

Component A: compound No. 1 with components B: DPX-84, DPX-47 and SK-23, etc.

Compound No. 1 as a component A is a compound prepared by the later-described Preparation example 1.

The compounding ratio between component A and component B in the herbicidal composition of the present invention is not strictly limited, and can be varied over a wide range depending on treatment areas, weeds, times, etc. set for application of the resultant final herbicidal composition, but it is generally suitable for mixing the latter component B in a ratio of 0.01 to 1,000 weight parts, preferably 0.1 to 500 weight parts per weight of the former component A. A further preferred mixing ratio can individually be determined depending on the kinds of components A and components B, among the above range. For example, when the above sulfonylurea derivatives of (12) to (15) (TH-913, DPX-84, NC-311 and DPX-47) are used as components B, it is proper to compound the latter components B in a ratio of 0.01 to 100 weight parts, preferably 0.1 to 5 weight parts per weight of the former components A.

When the above compound (6), i.e. SK-23 is used as component B, it is proper to mix the component B (SK-23) in a ratio of 0.01 to 100 weight parts, preferably 5 to 50 weight parts per weight of component A.

When a component C is further added to the above herbicidal composition, the mixing ratio is not strictly limited, either, and can be varied over a wide range depending on treatment areas, times, etc. set for application of the resultant final herbicidal composition.

When the composition of the present invention is actually used as a herbicide, the above active ingredients can be mixed with solid or liquid carriers, or a diluent, a surfactant and other auxiliaries for formulation, known per se, according to a method known per se, and formulated into formulates usually adopted for pesticides, for example granules, wettable powders, flowable, agents, etc.

Solid carriers usable in preparation of herbicides include, for example, clays represented by Kaolinites, montmorillonites, illites, polygroskites, etc., detailedly pyrophillite, atapulgite, sepiolite, kaolinite, bentonite, saponite, vermiculite, mica, talc, etc.; other inorganic substances such as gypsum, calcium carbonate, dolomite, diatom earth, calcite, magnesium lime, apatite, zeolite, silicic anhydride and synthetic calcium silicate; vegetable origin organic substances such as soybean meal, tobacco meal, walnut meal, wheat flour, sawdust, starches and crystalline cellulose; synthetic or natural high molecular compounds such as cumarone resins, petroleum resins, alkyd resins, poly(vinyl chloride), polyalkylene glycols, ketone resins, ester gum, copal gum and dammal gum; waxes such as carnauba wax and beeswax; urea; etc.

Suitable liquid carriers include, for example, paraffin or naphthene hydrocarbons such as kerosine, mineral oil, spindle oil and white oil; aromatic hydrocarbons such as xylene, ethylbenzene, cumene and methylnaphthalene; chlorinated hydrocarbons such as trichloroethylene, monochlorobenzene and o-chlorotoluene; ethers such as dioxane and tetrahydrofuran; ketones such as methyl ethyl ketone, diisobutyl ketone, cyclohexanone, acetophenone and isophorone; esters such as ethyl acetate, amyl acetate, ethylene glycol acetate, diethylene glycol acetate, dibutyl maleate and diethyl succinate; alcohols such as n-hexanol, ethylene glycol, diethylene glycol, cyclohexanol and benzyl alcohol; ether alcohols such as ethylene glycol ethyl ether, ethyl glycol phenyl ether, diethylene glycol ethyl ether and diethylene glycol butyl ether; polar solvents such as dimethylformamide and dimethyl sulfoxide; water; etc.

Surfactants and other auxiliaries can also be used further for the purposes of emulsification, dispersion, wetting, spreading and binding of the active ingredients, adjustment of disintegrability, stabilization of the active ingredient, improvement of fluidity, corrosion protection, etc.

All the nonionic, anionic, cationic and amphoteric surfactants can be used as the surfactants, but usually used are nonionic and/or anionic ones.

Suitable nonionic surfactants include, for example, a compound obtained by adding ethylene oxide through polymerization to a higher alcohol such as lauryl alcohol, stearyl alcohol or oleyl alcohol; a compound obtained by adding ethylene oxide through polymerization to an alkylphenol such as isooctylphenol or nonylphenol; a compound obtained by adding ethylene oxide through polymerization to an alkylnaphthol such as butylnaphthol or octylnaphthol; a compound obtained by adding ethylene oxide through polymerization to a higher fatty acid such as palmitic acid, stearic acid or oleic acid; a compound obtained by adding ethylene oxide through polymerization to an amine such as dodecylamine or stearamide; a higher fatty acid ester of a polyhydric alcohol such as sorbitan and a compound obtained by adding ethylene oxide through polymerization thereto; a compound obtained by adding through block polymerization ethylene oxide to propylene oxide; etc.

Suitable anionic surfactants include, for example, alkyl sulfate ester salts such as sodium lauryl sulfate and oleyl alcohol sulfate ester amine salts; alkylsulfonate salts such as sodium dioctyl sulfosuccinate and sodium 2-ethylhexenesulfonate; arylsulfonate salts such as sodium isopropylnaphthalenesulfonate, sodium methylenebisnaphthalenesulfonate, sodium ligninsulfonate and sodium dodecylbenzenesulfoante; etc.

There can also be used together for the composition of the present invention, mainly for the purpose of improving the performance of formulations and enhancement of herbicidal efficacy, higher molecular compounds such as casein, gelatin, albumin, glue, ligninsulfonate salts, alginate salts, gum arabic, carboxymethylcellulose, methylcellulose, hydroxyethylcellulose, polyvinylaldol, polyvinylpyrrolidone and polysaccharides; and other auxiliaries.

The above carriers and various auxiliaries can appropriately be used alone or in combination, in accordance with purposes, taking the forms of formulations, sites set for application, etc. into account.

The content of the effective ingredient in the composition of the present invention in various formulations thus obtained can be varied variously depending on formulations, but can, for example, be in the range of 0.01 to 99 % by weight, preferably 0.4 to 30% by weight.

In the case of wettable powder, it contains, for example, usually 0.5 to 90 % by weight of an active ingredient, the residual portion comprises a solid carrier, dispersing and wetting agents, and a protective colloid agent, and antiforming agent, etc. are added when needed.

In the case of a granule, it contains, for example, usually 0.01 to 35 % by weight of an active ingredient, and the residual portion comprises a solid carrier, a surfactant, etc. The active ingredient is either uniformly mixed with the solid carrier, or uniformly adheres to the surface of the solid carrier or is adsorbed on the surface, and the diameter of the granule can be in the range of about 0.2 to 1.5 mm.

In the case of a flowable formulate, it contains, for example, usually 0.5 to 50% by weight of an active ingredient, and 3 to 10% by weight of dispersing and wetting agents, and the residual portion comprises water, and a protective colloid agent, an antiseptic agent, an antiforming agent, etc. are added when needed.

The proper application dose of the composition of the present invention thus prepared cannot sweepingly be defined because of differences of weather conditions, solid conditions, formulations of chemicals, targeted crops, targeted weeds, time of application, methods for application, etc., but is within the range of 0.01 to 10 kg, preferably 0.01 to 2 kg per hectare in terms of the total amount of the active ingredients.

It is also possible, when needed, to use the composition of the present invention in mixing with other various chemicals such as insecticides, fungicides, plant growth regulators, herbicides and fertilizers.

The herbicidal composition of the present invention exhibits a high effect in low dose of active ingredients against wide-ranging weeds occurring in paddy fields, for example annual weeds such as *Echinochloa oryzicola* (common name: Early watergrass), *Monochoria vaginalis* (Japanese common name: Konagi), *Lindernia procumbens* (common name: Common falsepimpernel), *Cyperus microiria* (Japanese common name: Tamagayatsuri), *Scirpus Juncoides* (common name: Japanese bulrush) and *Alisma conaliculatum* (Japanese common name: Heraomodaka), and hard to control perennial weeds such as *Cyperus serotinus* (Japanese common name: Mizugayatsuri), *Sagittaria pygmaea* (Japanese common name: Urikawa) and *Eleocharis Kuroguwai* (Japanese common name: Kuroguwai); has extremely high safety on paddy rice; and does not cause any phytotoxicity, which becomes a problem, so long as it is used in a usual method. The herbicidal composition of the present invention also shows a high control effect against annual weeds occurring in fields such as barnyard grass, crab-grass and foxtail, and hard to control perennial weeds occurring in fields such as nut grass.

Its use time can optionally be chosen from the wide range from pre-transplantation of paddy rice to the initial stage of occurrence of weeds (about 20 days after the transplantation). Since complete weeds control is possible in one treatment of the herbicidal composition of the present invention, labor required for weed control can much be reduced.

The herbicidal composition of the present invention has merits of the high weed-control power of each effective ingredient and a strong synergistic effect, and thus it is possible to make the application amount of the effective ingredients extremely small, compared with usual herbicides. Therefore, it can be said that it has high safety on the environment and persons engaging in agriculture, and is a herbicide meeting the demands of the age.

EXAMPLES

The present invention is more specifically described below according to preparation examples, formulation examples and test examples.

Preparation example 1

Preparation of 6-methyl-3-[1-methyl-1-(3,5-dichlorophenyl)ethyl]-5-phenyl-2,3-dihydro-4H-1,3-oxazin-4-one (Compound No. 1):

1-Methyl-1-(3,5-dichlorophenyl)ethylamine (7.5 g) was gradually added to formalin (37% aqueous HCHO solution) (4.6 g) at room temperature. This mixture was subjected as it is to reaction for 7 hours. A saturated sodium bicarbonate solution was added to the reaction mixture, the resultant was extracted with ether and this organic layer was washed with saturated saline solution, and then dried over anhydrous sodium sulfate. The solvent was removed by evaporation under reduced pressure to obtain 8.6 g of N-methylene-1-methyl-1-(3,5-dichloro-phenyl)ethylamine as white crystals.

Then, a mixture of 5-phenyl-2,2,6-trimethyl-2H,4H-1,3-dioxin-4-one (0.65 g) and N-methylene-1-methyl-1-(3,5-dichlorophenyl)ethylamine (0.65 g) said above was refluxed at 150° C. for 30 minutes for reaction. The reaction mixture was subjected to recrystallization from a mixed solvent of hexane and ethyl acetate to obtain the captioned compound (0.90 g).

Preparation examples 2 to 7

Compound Nos. 2 to 7 shown in the following Table 1 were prepared by using the same procedure as described in the Preparation example 1.

The melting points and 'H-NMR peak values of the substances prepared is Preparation examples 1 to 7 are shown in Table 1.

TABLE 1

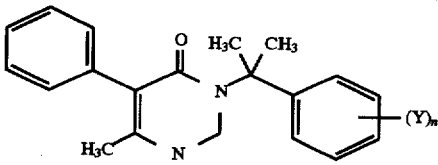

| Compound No. | (Y)n | N M R δ[ppm.] (300 MHz) solvent CDCl₃, TMS = 0 ppm. | Melting point (°C.) |
|---|---|---|---|
| 1 | 3-Cl, 5-Cl | 1.73(s, 6H), 1.93(s, 3H), 5.26(s, 2H), 7.19–7.35(m, 8H) | 148.0–150.5 |
| 2 | 3-Cl | 1.77(s, 6H), 1.91(s, 3H), 5.18(s, 2H), 7.10–7.42(m, 9H) | 66.5–68.5 |
| 3 | 3-F | 1.78(s, 6H), 1.91(s, 3H), 5.17(s, 2H), 6.88–6.96(m, 1H), 7.06–7.13(m, 1H), 7.17(d, 1H), 7.21–7.36(m, 6H) | 103.5–106.0 |
| 4 | 4-F | 1.80(s, 6H), 1.90(s, 3H), 5.12(s, 2H), 6.96–7.42(m, 9H) | 89.0–93.0 |
| 5 | 2-Cl | 1.86(s, 6H), 1.87(s, 3H), 5.33(s, 2H), 7.08–7.14(m, 1H), 7.17–7.31(m, 7H), 7.46–7.50(m, 1H) | 128.0–130.5 |
| 6 | 3-CH₃ | 1.81(s, 6H), 1.88(s, 3H), 2.36(s, 3H), 5.04(s, 2H), 6.95–7.40(m, 9H) | oily |
| 7 | 3-OCHF₂ | 1.78(s, 6H), 1.91(s, 3H), 5.20(s, 2H), 6.50(t. 1H), 6.94–6.99(m, 1H), 7.11–7.14(m, 1H), 7.19–7.36(m, 7H) | oily |

| Example 1 (emulsified concentrate) | |
|---|---|
| Component A: Compound No. 1 | 0.4% by weight |
| Component B: G-315 | 8% by weight |
| Polyoxyethylene styrylphenyl ether | 3% by weight |
| Calcium dodecylbenzenesulfonate | 3% by weight |
| Xylene | 85.6% by weight |

The above mixture was uniformly dissolved to obtain an emulsified concentrate formulate.

| Example 2 (wettable powder) | |
|---|---|
| Component A: Compound No. 1 | 0.4% by weight |
| Component B: G-315 | 8% by weight |
| Sodium ligninsulfonate | 3% by weight |

| Example 2 (wettable powder) | |
| --- | --- |
| Sodium dialkylnaphthalenesulfonate | 3% by weight |
| Kaolin | 85.6% by weight |

The above mixture was mixed well and ground to obtain a wettable powder formulate.

| Example 3 (flowable) | |
| --- | --- |
| Component A: Compound No. 1 | 0.4% by weight |
| Component B: MY-71 | 20% by weight |
| Polyoxyethylene nonylphenyl ether | 2% by weight |
| Sodium dioctyl sulfosuccinate | 2% by weight |
| Zansan gum | 0.2% by weight |
| Water | 75.4% by weight |

The above mixture was ground in wet system using a wet ball mill to obtain a flowable formulate.

| Example 4 (granule) | |
| --- | --- |
| Component A: Compound No. 1 | 0.13% by weight |
| Component B: MY-71 | 4% by weight |
| Sodium ligninsulfonate | 3% by weight |
| Sodium dialkylnaphthalenesulfonate | 3% by weight |
| Bentonite | 30% by weight |
| Talc | 59.87% by weight |

The above mixture was mixed well and ground, granulated by a granulator according to a conventional method, and dried to obtain a granule formulate.

| Example 5 (flowable) | |
| --- | --- |
| Component A: Compound No. 1 | 0.2% by weight |
| Component B: SK-23 | 20% by weight |
| Polyoxyethylene nonylphenyl ether | 2% by weight |
| Sodium dioctyl sulfosuccinate | 2% by weight |
| Zansan gum | 0.2% by weight |
| Water | 75.6% by weight |

The above mixture was ground in wet system using a wet ball mill to obtain a flowable formulate.

| Example 6 (granule) | |
| --- | --- |
| Component A: Compound No. 1 | 0.13% by weight |
| Component B: SK-23 | 6.67% by weight |
| Sodium ligninsulfonate | 3% by weight |
| Sodium dialkylnaphthalenesulfonate | 3% by weight |
| Bentonite | 30% by weight |
| Talc | 57.2% by weight |

The above mixture was mixed well and ground, granulated by a granulator according to a conventional method, and dried to obtain a granule formulate.

| Example 7 (wettable powder) | |
| --- | --- |
| Component A: Compound No. 1 | 0.4% by weight |
| Component B: CNP | 27% by weight |
| Sodium ligninsulfonate | 3% by weight |

| Example 7 (wettable powder) | |
| --- | --- |
| Sodium dialkylnaphthalenesulfonate | 3% by weight |
| Kaolin | 66.6% by weight |

The above mixture was mixed well and ground to obtain a wettable powder formulate.

| Example 8 (granule) | |
| --- | --- |
| Component A: Compound No. 1 | 0.13% by weight |
| Component B: CNP | 9% by weight |
| Sodium ligninsulfonate | 3% by weight |
| Sodium dialkylnaphthalenesulfonate | 3% by weight |
| Bentonite | 30% by weight |
| Talc | 54.87% by weight |

The above mixture was mixed well and ground, granulated by a granulator according to a conventional method, and dried to obtain a granule formulate.

| Example 9 (wettable powder) | |
| --- | --- |
| Component A: Compound No. 1 | 0.4% by weight |
| Component B: MC-79 | 20% by weight |
| Sodium ligninsulfonate | 3% by weight |
| Sodium dialkylnaphthalenesulfonate | 3% by weight |
| Kaolin | 73.6% by weight |

The above mixture was mixed well and ground to obtain a wettable powder formulate.

| Example 10 (granule) | |
| --- | --- |
| Component A: Compound No. 1 | 0.13% by weight |
| Component B: MC-79 | 6.67% by weight |
| Sodium ligninsulfonate | 3% by weight |
| Sodium dialkylnaphthalenesulfonate | 3% by weight |
| Bentonite | 30% by weight |
| Talc | 57.2% by weight |

The above mixture was mixed well and ground, granulated by a granulator according to a conventional method, and dried to obtain a granule formulate.

| Example 11 (flowable) | |
| --- | --- |
| Component A: Compound No. 1 | 0.2% by weight |
| Component B: MY-71 | 12% by weight |
| Component B: S-47 | 10% by weight |
| Polyoxyethylene nonylphenyl ether | 2% by weight |
| Sodium dioctyl sulfosuccinate | 2% by weight |
| Zansan gum | 0.2% by weight |
| Water | 73.4% by weight |

The above mixture was ground in wet system using a wet ball mill to obtain a flowable formulate.

| Example 12 (granule) | |
| --- | --- |
| Component A: Compound No. 1 | 0.13% by weight |
| Component B: MY-71 | 4% by weight |
| Component B: S-47 | 3.33% by weight |
| Sodium ligninsulfonate | 3% by weight |
| Sodium dialkylnaphthalenesulfonate | 3% by weight |

| Example 12 (granule) | |
|---|---|
| Bentonite | 30% by weight |
| Talc | 56.54% by weight |

The above mixture was mixed well and ground, granulated by a granulator according to a conventional method, and dried to obtain a granule formulate.

| Example 13 (flowable) | |
|---|---|
| Component A: Compound No. 1 | 0.3% by weight |
| Component B: MY-71 | 10% by weight |
| Component B: JC-940 | 10% by weight |
| Polyoxyethylene nonylphenyl ether | 2% by weight |
| Sodium dioctyl sulfosuccinate | 2% by weight |
| Zansan gum | 0.2% by weight |
| Water | 75.5% by weight |

The above mixture was ground in wet system using a wet ball mill to obtain a flowable formulate.

| Example 14 (granule) | |
|---|---|
| Component A: Compound No. 1 | 0.1% by weight |
| Component B: MY-71 | 3.3% by weight |
| Component B: JC-940 | 3.3% by weight |
| Sodium ligninsulfonate | 3% by weight |
| Sodium dialkylnaphthalenesulfonate | 3% by weight |
| Bentonite | 30% by weight |
| Talc | 58.3% by weight |

The above mixture was mixed well and ground, granulated by a granulator according to a conventional method, and dried to obtain a granule formulate.

| Example 15 (flowable) | |
|---|---|
| Component A: Compound No. 1 | 0.4% by weight |
| Component B: MY-71 | 10% by weight |
| Component B: MY-15 | 3% by weight |
| Component B: S-47 | 10% by weight |
| Polyoxyethylene nonylphenyl ether | 2% by weight |
| Sodium dioctyl sulfosuccinate | 2% by weight |
| Zansan gum | 0.2% by weight |
| Water | 72.4% by weight |

The above mixture was ground in wet system using a wet ball mill to obtain a flowable formulate.

| Example 16 (granule) | |
|---|---|
| Component A: Compound No. 1 | 0.13% by weight |
| Component B: MY-71 | 3.33% by weight |
| Component B: MY-15 | 1% by weight |
| Component B: S-47 | 3.34% by weight |
| Sodium ligninsulfonate | 3% by weight |
| Sodium dialkylnaphthalenesulfonate | 3% by weight |
| Bentonite | 30% by weight |
| Talc | 56.2% by weight |

The above mixture was mixed well and ground, granulated by a granulator according to a conventional method, and dried to obtain a granule formulate.

| Example 17 (wettable powder) | |
|---|---|
| Component A: Compound No. 1 | 0.4% by weight |
| Component B: MY-71 | 10% by weight |
| Component B: MY-15 | 3% by weight |
| Component B: NS-112 | 4.5% by weight |
| Sodium ligninsulfonate | 3% by weight |
| Sodium dialkylnaphthalenesulfonate | 3% by weight |
| Kaolin | 76.1% by weight |

The above mixture was mixed well and ground to obtain a wettable powder formulate.

| Example 18 (granule) | |
|---|---|
| Component A: Compound No. 1 | 0.13% by weight |
| Component B: MY-71 | 3.33% by weight |
| Component B: MY-15 | 1% by weight |
| Component B: NS-112 | 1.5% by weight |
| Sodium ligninsulfonate | 3% by weight |
| Sodium dialkylnaphthalenesulfonate | 3% by weight |
| Bentonite | 30% by weight |
| Talc | 58.04% by weight |

The above mixture was mixed well and ground, granulated by a granulator according to a conventional method, and dried to obtain a granule formulate.

| Comparative example 1 (flowable) | |
|---|---|
| Component A: Compound No. 1 | 0.8% by weight |
| Polyoxyethylene nonylphenyl ether | 2% by weight |
| Sodium dioctyl sulfosuccinate | 2% by weight |
| Zansan gum | 0.2% by weight |
| Water | 95% by weight |

The above mixture was ground in wet system using a wet ball mill to obtain a flowable formulate.

| Comparative example 2 (granule) | |
|---|---|
| Component A: Compound No. 1 | 0.27% by weight |
| Sodium ligninsulfonate | 3% by weight |
| Sodium dialkylnaphthalenesulfonate | 3% by weight |
| Bentonite | 30% by weight |
| Talc | 63.73% by weight |

The above mixture was mixed well and ground, granulated by a granulator according to a conventional method, and dried to obtain a granule formulate.

| Comparative example 3 (emulsified concentrate) | |
|---|---|
| Component A: Compound No. 1 | 0.8% by weight |
| Polyoxyethylene styrylphenyl ether | 3% by weight |
| Calcium dodecylbenzenesulfonate | 3% by weight |
| Xylene | 93.2% by weight |

The above mixture was uniformly mixed to obtain an emulsified concentrate formulate.

| Comparative example 4 (flowable) | |
|---|---|
| Component B: MY-71 | 10% by weight |
| Polyoxyethylene nonylphenyl ether | 2% by weight |

-continued

| | |
|---|---|
| Sodium dioctyl sulfosuccinate | 2% by weight |
| Zansan gum | 0.2% by weight |
| Water | 85.8% by weight |

The above mixture was ground in wet system using a wet ball mill to obtain a flowable formulate.

| Comparative example 5 (granule) | |
|---|---|
| Component B: MY-71 | 4% by weight |
| Sodium ligninsulfonate | 3% by weight |
| Sodium dialkylnaphthalenesulfonate | 3% by weight |
| Bentonite | 30% by weight |
| Talc | 60% by weight |

The above mixture was mixed well and ground, granulated by a granulator according to a conventional method, and dried to obtain a granule formulate.

| Comparative example 6 (flowable) | |
|---|---|
| Component B: MY-15 | 10% by weight |
| Polyoxyethylene nonylphenyl ether | 2% by weight |
| Sodium dioctyl sulfosuccinate | 2% by weight |
| Zansan gum | 0.2% by weight |
| Water | 85.8% by weight |

The above mixture was ground in wet system using a wet ball mill to obtain a flowable formulate.

| Comparative example 7 (granule) | |
|---|---|
| Component B: MY-15 | 2% by weight |
| Sodium ligninsulfonate | 3% by weight |
| Sodium dialkylnaphthalenesulfonate | 3% by weight |
| Bentonite | 30% by weight |
| Talc | 62% by weight |

The above mixture was mixed well and ground, granulated by a granulator according to a conventional method, and dried to obtain a granule formulate.

| Comparative example 8 (flowable) | |
|---|---|
| Component B: S-47 | 10% by weight |
| Polyoxyethylene nonylphenyl ether | 2% by weight |
| Zodium dioctyl sulfosuccinate | 2% by weight |
| Zansan gum | 0.2% by weight |
| Water | 85.8% by weight |

The above mixture was ground in wet system using a wet ball mill to obtain a flowable formulate.

| Comparative example 9 (granule) | |
|---|---|
| Component B: S-47 | 4% by weight |
| Sodium ligninsulfonate | 3% by weight |
| Sodium dialkylnaphthalenesulfonate | 3% by weight |
| Bentonite | 30% by weight |
| Talc | 60% by weight |

The above mixture was mixed well and ground, granulated by a granulator according to a conventional method, and dried to obtain a granule formulate.

| Comparative example 10 (wettable powder) | |
|---|---|
| Component B: NS-112 | 10% by weight |
| Sodium ligninsulfonate | 3% by weight |
| Sodium dialkylnaphthalenesulfonate | 3% by weight |
| Kaolin | 84% by weight |

The above mixture was uniformly mixed and ground to obtain a wettable powder formulate.

| Comparative example 11 (granule) | |
|---|---|
| Component B: NS-112 | 1.5% by weight |
| Sodium ligninsulfonate | 3% by weight |
| Sodium dialkylnaphthalenesulfonate | 3% by weight |
| Bentonite | 30% by weight |
| Talc | 62.5% by weight |

The above mixture was mixed well and ground, granulated by a granulator according to a conventional method, and dried to obtain a granule formulate.

| Comparative example 12 (flowable) | |
|---|---|
| Component B: SK-23 | 10% by weight |
| Polyoxyethylene nonylphenyl ether | 2% by weight |
| Sodium dioctyl sulfosuccinate | 2% by weight |
| Zansan gum | 0.2% by weight |
| Water | 85.8% by weight |

The above mixture was ground in wet system using a wet ball mill to obtain a flowable formulate.

| Comparative example 13 (granule) | |
|---|---|
| Component B: SK-23 | 1.5% by weight |
| Sodium ligninsulfonate | 3% by weight |
| Sodium dialkylnaphthalenesulfonate | 3% by weight |
| Bentonite | 30% by weight |
| Talc | 62.5% by weight |

The above mixture was mixed well and ground, granulated by a granulator according to a conventional method, and dried to obtain a granule formulate.

| Comparative example 14 (flowable) | |
|---|---|
| Component B: JC-940 | 10% by weight |
| Polyoxyethylene nonylphenyl ether | 2% by weight |
| Sodium dioctyl sulfosuccinate | 2% by weight |
| Zansan gum | 0.2% by weight |
| Water | 85.8% by weight |

The above mixture was ground in wet system using a wet ball mill to obtain a flowable formulate.

| Comparative example 15 (granule) | |
|---|---|
| Component B: JC-940 | 6% by weight |
| Sodium ligninsulfonate | 3% by weight |
| Sodium dialkylnaphthalenesulfonate | 3% by weight |
| Bentonite | 30% by weight |
| Talc | 58% by weight |

The above mixture was mixed well and ground, granulated by a granulator according to a conventional method, and dried to obtain a granule formulate.

| Comparative example 16 (wettable powder) | |
| --- | --- |
| Component B: CNP | 10% by weight |
| Sodium ligninsulfonate | 3% by weight |
| Sodium dialkylnaphthalenesulfonate | 3% by weight |
| Kaolin | 84% by weight |

The above mixture was uniformly mixed and ground to obtain a wettable powder formulate.

| Comparative example 17 (granule) | |
| --- | --- |
| Component B: CNP | 9% by weight |
| Sodium ligninsulfonate | 3% by weight |
| Sodium dialkylnaphthalenesulfonate | 3% by weight |
| Bentonite | 30% by weight |
| Talc | 55% by weight |

The above mixture was mixed well and ground, granulated by a granulator according to a conventional method, and dried to obtain a granule formulate.

| Comparative example 18 (wettable powder) | |
| --- | --- |
| Component B: MC-79 | 10% by weight |
| Sodium ligninsulfonate | 3% by weight |
| Sodium dialkylnaphthalenesulfonate | 3% by weight |
| Kaolin | 84% by weight |

The above mixture was uniformly mixed and ground to obtain a wettable powder formulate.

| Comparative example 19 (granule) | |
| --- | --- |
| Component B: MC-79 | 9% by weight |
| Sodium ligninsulfonate | 3% by weight |
| Sodium dialkylnaphthalenesulfonate | 3% by weight |
| Bentonite | 30% by weight |
| Talc | 57% by weight |

The above mixture was mixed well and ground, granulated by a granulator according to a conventional method, and dried to obtain a granule formulate.

| Comparative example 20 (wettable powder) | |
| --- | --- |
| Component B: MY-71 | 10% by weight |
| Sodium ligninsulfonate | 3% by weight |
| Sodium dialkylnaphthalenesulfonate | 3% by weight |
| Kaolin | 84% by weight |

The above mixture was uniformly mixed and ground to obtain a wettable powder formulate.

| Comparative example 21 (wettable powder) | |
| --- | --- |
| Component B: MY-15 | 10% by weight |
| Sodium ligninsulfonate | 3% by weight |
| Sodium dialkylnaphthalenesulfonate | 3% by weight |
| Kaolin | 84% by weight |

The above mixture was uniformly mixed and ground to obtain a wettable powder formulate.

| Comparative example 22 (emulsified concentrate) | |
| --- | --- |
| Component B: G-315 | 8% by weight |
| Polyoxyethylene styrylphenyl ether | 3% by weight |
| Calcium dodecylbenzenesulfonate | 3% by weight |
| Xylene | 86% by weight |

The above mixture was uniformly mixed to obtain an emulsified concentrate formulate.

| Comparative example 23 (wettable powder) | |
| --- | --- |
| Component B: G-315 | 8% by weight |
| Sodium ligninsulfonate | 3% by weight |
| Sodium dialkylnaphthalenesulfonate | 3% by weight |
| Kaolin | 86% by weight |

The above mixture was uniformly mixed and ground to obtain a wettable powder formulate.

| Comparative example 24 (wettable powder) | |
| --- | --- |
| Component A: Compound No. 1 | 1% by weight |
| Sodium ligninsulfonate | 3% by weight |
| Sodium dialkylnaphthalenesulfonate | 3% by weight |
| Kaolin | 93% by weight |

The above mixture was uniformly mixed and ground to obtain a wettable powder formulate.

| Comparative example 25 (wettable powder) | |
| --- | --- |
| Component B: G32911 | 4.5% by weight |
| Sodium ligninsulfonate | 3% by weight |
| Sodium dialkylnaphthalenesulfonate | 3% by weight |
| Kaolin | 89.5% by weight |

The above mixture was uniformly mixed and ground to obtain a wettable powder formulate.

| Comparative example 26 (granule) | |
| --- | --- |
| Component B: G32911 | 1.5% by weight |
| Sodium ligninsulfonate | 3% by weight |
| Sodium dialkylnaphthalenesulfonate | 3% by weight |
| Bentonite | 30% by weight |
| Talc | 62.5% by weight |

The above mixture was mixed well and ground, granulated by a granulator according to a conventional method, and dried to obtain a granule formulate.

| Example 19 (wettable powder) | |
| --- | --- |
| Component A: Compound No. 1 | 0.4% by weight |
| Component B: G32911 | 4.5% by weight |
| Sodium ligninsulfonate | 3% by weight |
| Sodium dialkylnaphthalenesulfonate | 3% by weight |
| Kaolin | 89.1% by weight |

The above mixture was uniformly mixed and ground to obtain a wettable powder formulate.

| Example 20 (granule) | |
| --- | --- |
| Component A: Compound No. 1 | 0.13% by weight |
| Component B: G32911 | 1.5% by weight |
| Sodium ligninsulfonate | 3% by weight |
| Sodium dialkylnaphthalenesulfonate | 3% by weight |
| Bentonite | 30% by weight |
| Talc | 62.37% by weight |

The above mixture was mixed well and ground, granulated by a granulator according to a conventional method, and dried to obtain a granule formulate.

| Comparative example 27 (wettable powder) | |
| --- | --- |
| Component B: CG-7103 | 3.3% by weight |
| Sodium ligninsulfonate | 3% by weight |
| Sodium dialkylnaphthalenesulfonate | 3% by weight |
| Kaolin | 90.7% by weight |

The above mixture was uniformly mixed and ground to obtain a wettable powder formulate.

| Comparative example 28 (granule) | |
| --- | --- |
| Component B: CG-7103 | 1.1% by weight |
| Sodium ligninsulfonate | 3% by weight |
| Sodium dialkylnaphthalenesulfonate | 3% by weight |
| Bentonite | 30% by weight |
| Talc | 62.9% by weight |

The above mixture was mixed well and ground, granulated by a granulator according to a conventional method, and dried to obtain a granule formulate.

| Example 21 (wettable powder) | |
| --- | --- |
| Component A: Compound No. 1 | 0.4% by weight |
| Component B: CG-7103 | 3.3% by weight |
| Sodium ligninsulfonate | 3% by weight |
| Sodium dialkylnaphthalenesulfonate | 3% by weight |
| Kaolin | 90.3% by weight |

The above mixture was uniformly mixed and ground to obtain a wettable powder formulate.

| Example 22 (granule) | |
| --- | --- |
| Component A: Compound No. 1 | 0.13% by weight |
| Component B: CG-7103 | 1.1% by weight |
| Sodium ligninsulfonate | 3% by weight |
| Sodium dialkylnaphthalenesulfonate | 3% by weight |
| Bentonite | 30% by weight |
| Talc | 62.77% by weight |

The above mixture was mixed well and ground, granulated by a granulator according to a conventional method, and dried to obtain a granule formulate.

| Comparative example 29 (granule) | |
| --- | --- |
| Component A: Compound No. 1 | 0.2% by weight |
| Sodium ligninsulfonate | 3% by weight |
| Sodium dialkylnaphthalenesulfonate | 3% by weight |
| Bentonite | 30% by weight |
| Talc | 63.8% by weight |

The above mixture was mixed well and ground, granulated by a granulator according to a conventional method, and dried to obtain a granule formulate.

| Comparative example 30 (granule) | |
| --- | --- |
| Component B: TH-913 | 0.3% by weight |
| Sodium ligninsulfonate | 3% by weight |
| Sodium dialkylnaphthalenesulfonate | 3% by weight |
| Bentonite | 30% by weight |
| Talc | 63.7% by weight |

The above mixture was mixed well and ground, granulated by a granulator according to a conventional method, and dried to obtain a granule formulate.

| Comparative example 31 (granule) | |
| --- | --- |
| Component B: SK-23 | 5% by weight |
| Sodium ligninsulfonate | 3% by weight |
| Sodium dialkylnaphthalenesulfonate | 3% by weight |
| Bentonite | 30% by weight |
| Talc | 59% by weight |

The above mixture was mixed well and ground, granulated by a granulator according to a conventional method, and dried to obtain a granule formulate.

| Example 23 (granule) | |
| --- | --- |
| Component A: Compound No. 1 | 0.2% by weight |
| Component B: TH-913 | 0.3% by weight |
| Sodium ligninsulfonate | 3% by weight |
| Sodium dialkylnaphthalenesulfonate | 3% by weight |
| Bentonite | 30% by weight |
| Talc | 63.5% by weight |

The above mixture was mixed well and ground, granulated by a granulator according to a conventional method, and dried to obtain a granule formulate.

| Example 24 (granule) | |
| --- | --- |
| Component A: Compound No. 1 | 0.2% by weight |
| Component B: TH-913 | 0.3% by weight |
| Component B: SK-23 | 5% by weight |
| Sodium ligninsulfonate | 3% by weight |
| Sodium dialkylnaphthalenesulfonate | 3% by weight |
| Bentonite | 30% by weight |
| Talc | 58.5% by weight |

The above mixture was mixed well and ground, granulated by a granulator according to a conventional method, and dried to obtain a granule formulate.

| Comparative example 32 (flowable) | |
| --- | --- |
| Component A: Compound No. 1 | 0.4% by weight |
| Polyoxyethylene nonylphenyl ether | 2% by weight |

| Comparative example 32 (flowable) | |
| --- | --- |
| Sodium dioctyl sulfosuccinate | 2% by weight |
| Zansan gum | 0.2% by weight |
| Talc | 95.4% by weight |

The above mixture was ground in wet system using a wet ball mill to obtain a flowable formulate.

| Comparative example 33 (flowable) | |
| --- | --- |
| Component B: TH-913 | 0.9% by weight |
| Polyoxyethylene nonylphenyl ether | 2% by weight |
| Sodium dioctyl sulfosuccinate | 2% by weight |
| Zansan gum | 0.2% by weight |
| Water | 94.9% by weight |

The above mixture was ground in wet system using a wet ball mill to obtain a flowable formulate.

| Comparative example 34 (flowable) | |
| --- | --- |
| Component B: SK-23 | 15% by weight |
| Polyoxyethylene nonylphenyl ether | 2% by weight |
| Sodium dioctyl sulfosuccinate | 2% by weight |
| Zansan gum | 0.2% by weight |
| Water | 80.8% by weight |

The above mixture was ground in wet system using a wet ball mill to obtain a flowable formulate.

| Example 25 (flowable) | |
| --- | --- |
| Component A: Compound No. 1 | 0.4% by weight |
| Component B: TH-913 | 0.9% by weight |
| Polyoxyethylene nonylphenyl ether | 2% by weight |
| Sodium dioctyl sulfosuccinate | 2% by weight |
| Zansan gum | 0.2% by weight |
| Water | 94.5% by weight |

The above mixture was ground in wet system using a wet ball mill to obtain a flowable formulate.

| Example 26 (flowable) | |
| --- | --- |
| Component A: Compound No. 1 | 0.4% by weight |
| Component B: TH-913 | 0.9% by weight |
| Component B: SK-23 | 15% by weight |
| Polyoxyethylene nonylphenyl ether | 2% by weight |
| Sodium dioctyl sulfosuccinate | 2% by weight |
| Zansan gum | 0.2% by weight |
| Water | 79.5% by weight |

The above mixture was ground in wet system using a wet ball mill to obtain a flowable formulate.

| Example 27 (wettable powder) | |
| --- | --- |
| Component A: Compound No. 1 | 0.54% by weight |
| Component B: TH-913 | 0.6% by weight |
| Sodium ligninsulfonate | 3% by weight |
| Sodium dialkylnaphthalenesulfonate | 3% by weight |
| Kaolin | 92.86% by weight |

The above mixture was uniformly mixed and ground to obtain a wettable powder formulate.

| Example 28 (wettable powder) | |
| --- | --- |
| Component A: Compound No. 1 | 0.54% by weight |
| Component B: TH-913 | 0.6% by weight |
| Component B: SK-23 | 10% by weight |
| Sodium ligninsulfonate | 3% by weight |
| Sodium dialkylnaphthalenesulfonate | 3% by weight |
| Kaolin | 82.86% by weight |

The above mixture was uniformly mixed and ground to obtain a wettable powder formulate.

| Comparative example 35 (granule) | |
| --- | --- |
| Component A: Compound No. 1 | 0.27% by weight |
| Sodium ligninsulfonate | 3% by weight |
| Sodium dialkylnaphthalenesulfonate | 3% by weight |
| Bentonite | 30% by weight |
| Talc | 63.73% by weight |

The above mixture was mixed well and ground, granulated by a granulator according to a conventional method, and dried to obtain a granule formulate.

| Comparative example 36 (granule) | |
| --- | --- |
| Component B: DPX-84 | 0.17% by weight |
| Sodium ligninsulfonate | 3% by weight |
| Sodium dialkylnaphthalenesulfonate | 3% by weight |
| Bentonite | 30% by weight |
| Talc | 63.83% by weight |

The above mixture was mixed well and ground, granulated by a granulator according to a conventional method, and dried to obtain a granule formulate.

| Comparative example 37 (granule) | |
| --- | --- |
| Component B: SK-23 | 1.5% by weight |
| Sodium ligninsulfonate | 3% by weight |
| Sodium dialkylnaphthalenesulfonate | 3% by weight |
| Bentonite | 30% by weight |
| Talc | 62.5% by weight |

The above mixture was mixed well and ground, granulated by a granulator according to a conventional method, and dried to obtain a granule formulate.

| Example 29 (granule) | |
| --- | --- |
| Component A: Compound No. 1 | 0.27% by weight |
| Component B: DPX-84 | 0.17% by weight |
| Sodium ligninsulfonate | 3% by weight |
| Sodium dialkylnaphthalenesulfonate | 3% by weight |
| Bentonite | 30% by weight |
| Talc | 63.56% by weight |

The above mixture was mixed well and ground, granulated by a granulator according to a conventional method, and dried to obtain a granule formulate.

| Example 30 (granule) | |
| --- | --- |
| Component A: Compound No. 1 | 0.27% by weight |
| Component B: DPX-84 | 1.17% by weight |
| Component B: SK-23 | 1.5% by weight |
| Sodium ligninsulfonate | 3% by weight |
| Sodium dialkylnaphthalenesulfonate | 3% by weight |
| Bentonite | 30% by weight |
| Talc | 62.06% by weight |

The above mixture was mixed well and ground, granulated by a granulator according to a conventional method, and dried to obtain a granule formulate.

| Comparative example 38 (flowable) | |
| --- | --- |
| Component A: Compound No. 1 | 0.54% by weight |
| Polyoxyethylene nonylphenyl ether | 2% by weight |
| Sodium dioctyl sulfosuccinate | 2% by weight |
| Zansan gum | 0.2% by weight |
| Water | 95.26% by weight |

The above mixture was ground in wet system using a wet ball mill to obtain a flowable formulate.

| Comparative example 39 (flowable) | |
| --- | --- |
| Component B: DPX-84 | 0.34% by weight |
| Polyoxyethylene nonylphenyl ether | 2% by weight |
| Sodium dioctyl sulfosuccinate | 2% by weight |
| Zansan gum | 0.2% by weight |
| Water | 95.46% by weight |

The above mixture was ground in wet system using a wet ball mill to obtain a flowable formulate.

| Comparative example 40 (flowable) | |
| --- | --- |
| Component B: SK-23 | 3% by weight |
| Polyoxyethylene nonylphenyl ether | 2% by weight |
| Sodium dioctyl sulfosuccinate | 2% by weight |
| Zansan gum | 0.2% by weight |
| Water | 92.8% by weight |

The above mixture was ground in wet system using a wet ball mill to obtain a flowable formulate.

| Example 31 (flowable) | |
| --- | --- |
| Component A: Compound No. 1 | 0.54% by weight |
| Component B: DPX-84 | 0.34% by weight |
| Polyoxyethylene nonylphenyl ether | 2% by weight |
| Sodium dioctyl sulfosuccinate | 2% by weight |
| Zansan gum | 0.2% by weight |
| Water | 94.92% by weight |

The above mixture was ground in wet system using a wet ball mill to obtain a flowable formulate.

| Example 32 (flowable) | |
| --- | --- |
| Component A: Compound No. 1 | 0.54% by weight |
| Component B: DPX-84 | 0.34% by weight |
| Component B: SK-23 | 3% by weight |
| Polyoxyethylene nonylphenyl ether | 2% by weight |
| Sodium dioctyl sulfosuccinate | 2% by weight |
| Zansan gum | 0.2% by weight |
| Water | 91.92% by weight |

The above mixture was ground in wet system using a wet ball mill to obtain a flowable formulate.

| Example 33 (wettable powder) | |
| --- | --- |
| Component A: Compound No. 1 | 1% by weight |
| Component B: DPX-84 | 0.8% by weight |
| Sodium ligninsulfonate | 3% by weight |
| Sodium dialkylnaphthalenesulfonate | 3% by weight |
| Kaolin | 92.2% by weight |

The above mixture was uniformly mixed and ground to obtain a wettable powder formulate.

| Example 34 (wettable powder) | |
| --- | --- |
| Component A: Compound No. 1 | 1% by weight |
| Component B: DPX-84 | 0.8% by weight |
| Component B: SK-23 | 10% by weight |
| Sodium ligninsulfonate | 3% by weight |
| Sodium dialkylnaphthalenesulfonate | 3% by weight |
| Kaolin | 82.2% by weight |

The above mixture was uniformly mixed and ground to obtain a wettable powder formulate.

| Comparative example 41 (granule) | |
| --- | --- |
| Component B: NC-311 | 0.07% by weight |
| Sodium ligninsulfonate | 3% by weight |
| Sodium dialkylnaphthalenesulfonate | 3% by weight |
| Bentonite | 30% by weight |
| Talc | 63.93% by weight |

The above mixture was mixed well and ground, granulated by a granulator according to a conventional method, and dried to obtain a granule formulate.

| Example 35 (granule) | |
| --- | --- |
| Component A: Compound No. 1 | 0.27% by weight |
| Component B: NC-311 | 0.07% by weight |
| Sodium ligninsulfonate | 3% by weight |
| Sodium dialkylnaphthalenesulfonate | 3% by weight |
| Bentonite | 30% by weight |
| Talc | 63.66% by weight |

The above mixture was mixed well and ground, granulated by a granulator according to a conventional method, and dried to obtain a granule formulate.

| Example 36 (granule) | |
| --- | --- |
| Component A: Compound No. 1 | 0.27% by weight |
| Component B: NC-311 | 0.07% by weight |
| Component B: SK-23 | 1.5% by weight |
| Sodium ligninsulfonate | 3% by weight |
| Sodium dialkylnaphthalenesulfonate | 3% by weight |

Example 36 (granule)

| | |
|---|---|
| Bentonite | 30% by weight |
| Talc | 62.16% by weight |

The above mixture was mixed well and ground, granulated by a granulator according to a conventional method, and dried to obtain a granule formulate.

Comparative example 42 (flowable)

| | |
|---|---|
| Component B: NC-311 | 0.14% by weight |
| Polyoxyethylene nonylphenyl ether | 2% by weight |
| Sodium dioctyl sulfosuccinate | 2% by weight |
| Zansan gum | 0.2% by weight |
| Water | 95.66% by weight |

The above mixture was ground in wet system using a wet ball mill to obtain a flowable formulate.

Example 37 (flowable)

| | |
|---|---|
| Component A: Compound No. 1 | 0.54% by weight |
| Component B: NC-311 | 0.14% by weight |
| Polyoxyethylene nonylphenyl ether | 2% by weight |
| Sodium dioctyl sulfosuccinate | 2% by weight |
| Zansan gum | 0.2% by weight |
| Water | 95.12% by weight |

The above mixture was ground in wet system using a wet ball mill to obtain a flowable formulate.

Example 38 (flowable)

| | |
|---|---|
| Component A: Compound No. 1 | 0.54% by weight |
| Component B: NC-311 | 0.14% by weight |
| Component B: SK-23 | 3% by weight |
| Polyoxyethylene nonylphenyl ether | 2% by weight |
| Sodium dioctyl sulfosuccinate | 2% by weight |
| Zansan gum | 0.2% by weight |
| Water | 91.92% by weight |

The above mixture was ground in wet system using a wet ball mill to obtain a flowable formulate.

Example 39 (wettable powder)

| | |
|---|---|
| Component A: Compound No. 1 | 0.5% by weight |
| Component B: NC-311 | 0.2% by weight |
| Sodium ligninsulfonate | 3% by weight |
| Sodium dialkylnaphthalenesulfonate | 3% by weight |
| Kaolin | 93.3% by weight |

The above mixture was uniformly mixed and ground to obtain a wettable powder formulate.

Example 40 (wettable powder)

| | |
|---|---|
| Component A: Compound No. 1 | 0.5% by weight |
| Component B: NC-311 | 0.2% by weight |
| Component B: SK-23 | 5% by weight |
| Sodium ligninsulfonate | 3% by weight |
| Sodium dialkylnaphthalenesulfonate | 3% by weight |
| Kaolin | 88.3% by weight |

The above mixture was uniformly mixed and ground to obtain a wettable powder formulate.

Comparative example 43 (granule)

| | |
|---|---|
| Component B: DPX-84 | 0.1% by weight |
| Sodium ligninsulfonate | 3% by weight |
| Sodium dialkylnaphthalenesulfonate | 3% by weight |
| Bentonite | 30% by weight |
| Talc | 63.9% by weight |

The above mixture was mixed well and ground, granulated by a granulator according to a conventional method, and dried to obtain a granule formulate.

Comparative example 44 (granule)

| | |
|---|---|
| Component B: DPX-47 | 0.22% by weight |
| Sodium ligninsulfonate | 3% by weight |
| Sodium dialkylnaphthalenesulfonate | 3% by weight |
| Bentonite | 30% by weight |
| Talc | 63.98% by weight |

The above mixture was mixed well and ground, granulated by a granulator according to a conventional method, and dried to obtain a granule formulate.

Comparative example 45 (granule)

| | |
|---|---|
| Component B: SK-23 | 1.5% by weight |
| Sodium ligninsulfonate | 3% by weight |
| Sodium dialkylnaphthalenesulfonate | 3% by weight |
| Bentonite | 30% by weight |
| Talc | 62.5% by weight |

The above mixture was mixed well and ground, granulated by a granulator according to a conventional method, and dried to obtain a granule formulate.

Example 41 (granule)

| | |
|---|---|
| Component A: Compound No. 1 | 0.2% by weight |
| Component B: DPX-84 | 0.1% by weight |
| Component B: DPX-47 | 0.02% by weight |
| Sodium ligninsulfonate | 3% by weight |
| Sodium dialkylnaphthalenesulfonate | 3% by weight |
| Bentonite | 30% by weight |
| Talc | 63.68% by weight |

The above mixture was mixed well and ground, granulated by a granulator according to a conventional method, and dried to obtain a granule formulate.

Example 42 (granule)

| | |
|---|---|
| Component A: Compound No. 1 | 0.2% by weight |
| Component B: DPX-84 | 0.1% by weight |
| Component B: DPX-47 | 0.02% by weight |
| Component B: SK-23 | 1.5% by weight |
| Sodium ligninsulfonate | 3% by weight |
| Sodium dialkylnaphthalenesulfonate | 3% by weight |
| Bentonite | 30% by weight |
| Talc | 62.18% by weight |

The above mixture was mixed well and ground, granulated by a granulator according to a conventional method, and dried to obtain a granule formulate.

| Comparative example 46 (flowable) | |
| --- | --- |
| Component A: Compound No. 1 | 0.6% by weight |
| Polyoxyethylene nonylphenyl ether | 2% by weight |
| Sodium dioctyl sulfosuccinate | 2% by weight |
| Zansan gum | 0.2% by weight |
| Water | 95.2% by weight |

The above mixture was ground in wet system using a wet ball mill to obtain a flowable formulate.

| Comparative example 47 (flowable) | |
| --- | --- |
| Component B: DPX-84 | 0.3% by weight |
| Polyoxyethylene nonylphenyl ether | 2% by weight |
| Sodium dioctyl sulfosuccinate | 2% by weight |
| Zansan gum | 0.2% by weight |
| Water | 95.5% by weight |

The above mixture was ground in wet system using a wet ball mill to obtain a flowable formulate.

| Comparative example 48 (flowable) | |
| --- | --- |
| Component B: DPX-47 | 0.06% by weight |
| Polyoxyethylene nonylphenyl ether | 2% by weight |
| Sodium dioctyl sulfosuccinate | 2% by weight |
| Zansan gum | 0.2% by weight |
| Water | 95.74% by weight |

The above mixture was ground in wet system using a wet ball mill to obtain a flowable formulate.

| Comparative example 49 (flowable) | |
| --- | --- |
| Component B: SK-23 | 4.5% by weight |
| Polyoxyethylene nonylphenyl ether | 2% by weight |
| Sodium dioctyl sulfosuccinate | 2% by weight |
| Zansan gum | 0.2% by weight |
| Water | 91.3% by weight |

The above mixture was ground in wet system using a wet ball mill to obtain a flowable formulate.

| Example 43 (flowable) | |
| --- | --- |
| Component A: Compound No. 1 | 0.6% by weight |
| Component B: DPX-84 | 0.3% by weight |
| Component B: DPX-47 | 0.06% by weight |
| Polyoxyethylene nonylphenyl ether | 2% by weight |
| Sodium dioctyl sulfosuccinate | 2% by weight |
| Zansan gum | 0.2% by weight |
| Water | 94.84% by weight |

The above mixture was ground in wet system using a wet ball mill to obtain a flowable formulate.

| Example 44 (flowable) | |
| --- | --- |
| Component A: Compound No. 1 | 0.6% by weight |
| Component B: DPX-84 | 0.3% by weight |
| Component B: DPX-47 | 0.06% by weight |
| Component B: SK-23 | 4.5% by weight |
| Polyoxyethylene nonylphenyl ether | 2% by weight |
| Sodium dioctyl sulfosuccinate | 2% by weight |
| Zansan gum | 0.2% by weight |
| Water | 90.34% by weight |

The above mixture was ground in wet system using a wet ball mill to obtain a flowable formulate.

| Example 45 (wettable powder) | |
| --- | --- |
| Component A: Compound No. 1 | 1% by weight |
| Component B: DPX-84 | 0.8% by weight |
| Component B: DPX-47 | 0.06% by weight |
| Sodium ligninsulfonate | 3% by weight |
| Sodium dialkylnaphthalenesulfonate | 3% by weight |
| Kaolin | 92.14% by weight |

The above mixture was uniformly mixed and ground to obtain a wettable powder formulate.

| Example 46 (wettable powder) | |
| --- | --- |
| Component A: Compound No. 1 | 1% by weight |
| Component B: DPX-84 | 0.8% by weight |
| Component B: DPX-47 | 0.06% by weight |
| Component B: SK-23 | 10% by weight |
| Sodium ligninsulfonate | 3% by weight |
| Sodium dialkylnaphthalenesulfonate | 3% by weight |
| Kaolin | 82.14% by weight |

The above mixture was uniformly mixed and ground to obtain a wettable powder formulate.

The effects of the herbicidal composition of the present invention are described below according to test examples.

Test example 1

(pre-transplanting treatment)

Portions of paddy field soil and portions of a compound fertilizer were put in Wagner pots having an area of 1/5,000 a, respectively, and an appropriate amount each of water was added, followed by sufficient mixing to give a sort of paddy fields. The formulations prepared in the above examples and comparative examples were applied thereto, respectively, so that the doses of the active ingredients became those shown in Tables 2 to 10, respectively. Two two-leaf stage paddy rice seedlings grown in advance in a greenhouse were transplanted per pot with two plants at one spot, certain amounts each of seeds of barnyard grass, konagi, azena and hotarui were sown per pot, certain amounts each of tubers of urikawa and mizugayatsuri were planted per pot, and water was poured in each pot to a water depth of 3 cm.

Herbicidal effects on these weeds and phytotoxicity on the paddy rice were assessed 30 days after the chemical treatment in accordance with the following criteria.

| Grade | Herbicidal rate (%) | Mark | Degree of phytotoxicity |
|---|---|---|---|
| 5 | 100 | x | withered |
| 4 | over 80, under 100 | +++ | large injury |
| 3 | over 60, 80 or less | ++ | middle injury |
| 2 | over 40, 60 or less | + | small injury |
| 1 | over 20, 40 or less | ± | slight injury |
| 0 | 0 or more, 20 or less | − | no injury |

The results are shown in the following tables 2 to 10.

TABLE 2

(pre-transplanting treatment-1)

| Test agent | Dose of active ingredient g ai/ha Component A | Component B | Herbicidal effect Hie *1 | Konagi *2 | Azena *3 | Hotarui *4 | Urikawa *5 | Mizugayatsuri *6 | Phytotoxicity on paddy rice |
|---|---|---|---|---|---|---|---|---|---|
| Component A: Compound No. 1 | 5 | | 4 | 4 | 3 | 3 | 0 | 1 | — |
| (Emulsified concentrate of | 10 | | 5 | 5 | 4 | 4 | 0 | 2 | — |
| Comparative example 3) | 20 | | 5 | 5 | 4 | 4 | 1 | 3 | — |
| Component B: G-315 | | 100 | 2 | 1 | 2 | 0 | 0 | 1 | — |
| (Emulsified concentrate of | | 200 | 3 | 2 | 3 | 1 | 0 | 2 | — |
| Comparative example 22) | | 400 | 4 | 4 | 5 | 2 | 1 | 3 | — |
| Composition of the present | 5 | 100 | 5 | 5 | 5 | 5 | 4 | 5 | — |
| invention | 10 | 200 | 5 | 5 | 5 | 5 | 5 | 5 | — |
| (Emulsified concentrate of | 20 | 400 | 5 | 5 | 5 | 5 | 5 | 5 | — |
| Example 1) | | | | | | | | | |
| Not treated | | | 0 | 0 | 0 | 0 | 0 | 0 | — |
| Component A: Compound No. 1 | 5 | | 4 | 4 | 3 | 3 | 0 | 1 | — |
| (Wettable powder of | 10 | | 5 | 5 | 4 | 4 | 0 | 2 | — |
| Comparative example 24) | 20 | | 5 | 5 | 4 | 4 | 1 | 3 | — |
| Component B: G-315 | | 100 | 2 | 1 | 1 | 0 | 0 | 1 | — |
| (Wettable powder of | | 200 | 3 | 2 | 3 | 1 | 0 | 2 | — |
| Comparative example 23) | | 400 | 4 | 5 | 4 | 2 | 1 | 3 | — |
| Composition of the present | 5 | 100 | 5 | 5 | 5 | 5 | 4 | 5 | — |
| invention | 10 | 200 | 5 | 5 | 5 | 5 | 5 | 5 | — |
| (Wettable powder of | 20 | 400 | 5 | 5 | 5 | 5 | 5 | 5 | — |
| Example 2) | | | | | | | | | |
| Not treated | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 3

(pre-transplanting treatment-2)

| Test agent | Dose of active ingredient g ai/ha Component A | Component B | Herbicidal effect Hie *1 | Konagi *2 | Azena *3 | Hotarui *4 | Urikawa *5 | Mizugayatsuri *6 | Phytotoxicity on paddy rice |
|---|---|---|---|---|---|---|---|---|---|
| Component A: Compound No. 1 | 5 | | 5 | 4 | 3 | 3 | 0 | 1 | — |
| (Flowable of Comparative | 10 | | 5 | 5 | 4 | 4 | 0 | 2 | — |
| example 1) | 20 | | 5 | 5 | 4 | 4 | 1 | 3 | — |
| Component B: MY-71 | | 250 | 0 | 3 | 3 | 0 | 3 | 2 | — |
| (Flowable of Comparative | | 500 | 0 | 4 | 4 | 1 | 4 | 3 | — |
| example 4) | | 1000 | 1 | 5 | 5 | 4 | 5 | 3 | — |

TABLE 3-continued (pre-transplanting treatment-2)

| Test agent | Dose of active ingredient g ai/ha | | Herbicidal effect | | | | | | Phytotoxicity on paddy rice |
|---|---|---|---|---|---|---|---|---|---|
| | Component A | Component B | Hie *1 | Konagi *2 | Azena *3 | Hotarui *4 | Urikawa *5 | Mizugayatsuri *6 | |
| Composition of the present invention (Flowable of Example 3) | 5 | 250 | 5 | 5 | 5 | 5 | 5 | 5 | — |
| | 10 | 500 | 5 | 5 | 5 | 5 | 5 | 5 | — |
| | 20 | 1000 | 5 | 5 | 5 | 5 | 5 | 5 | — |
| Not treated | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 4

(pre-transplanting treatment-3)

| Test agent | Dose of active ingredient g ai/ha | | Herbicidal effect | | | | | | Phytotoxicity on paddy rice |
|---|---|---|---|---|---|---|---|---|---|
| | Component A | Component B | Hie *1 | Konagi *2 | Azena *3 | Hotarui *4 | Urikawa *5 | Mizugayatsuri *6 | |
| Component A: Compound No. 1 (Flowable of Comparative example 1) | 5 | | 5 | 4 | 3 | 3 | 0 | 1 | — |
| | 10 | | 5 | 5 | 4 | 4 | 0 | 2 | — |
| | 20 | | 5 | 5 | 4 | 4 | 1 | 3 | — |
| Component B: SK-23 (Flowable of Comparative example 12) | | 250 | 1 | 1 | 1 | 2 | 0 | 3 | — |
| | | 1000 | 2 | 2 | 1 | 3 | 1 | 4 | — |
| | | 2000 | 3 | 4 | 2 | 4 | 1 | 5 | — |
| Composition of the present invention (Flowable of Example 5) | 5 | 250 | 5 | 5 | 5 | 5 | 4 | 5 | — |
| | 10 | 1000 | 5 | 5 | 5 | 5 | 4 | 5 | — |
| | 20 | 2000 | 5 | 5 | 5 | 5 | 5 | 5 | — |
| Not treated | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 5

(pre-transplanting treatment-4)

| Test agent | Dose of active ingredient g ai/ha | | Herbicidal effect | | | | | | Phytotoxicity on paddy rice |
|---|---|---|---|---|---|---|---|---|---|
| | Component A | Component B | Hie *1 | Konagi *2 | Azena *3 | Hotarui *4 | Urikawa *5 | Mizugayatsuri *6 | |
| Component A: Compound No. 1 (Wettable powder of Comparative example 24) | 5 | | 5 | 4 | 3 | 3 | 0 | 1 | — |
| | 10 | | 5 | 5 | 4 | 4 | 0 | 2 | — |
| | 20 | | 5 | 5 | 4 | 4 | 1 | 3 | — |
| Component B: CNP (Wettable powder of | | 675 | 2 | 3 | 3 | 2 | 0 | 0 | — |
| | | 1350 | 3 | 3 | 4 | 4 | 0 | 0 | — |

TABLE 5-continued (pre-transplanting treatment-4)

| Test agent | Dose of active ingredient g ai/ha | | Herbicidal effect | | | | | | Phytotoxicity on paddy rice |
|---|---|---|---|---|---|---|---|---|---|
| | Component A | Component B | Hie *1 | Konagi *2 | Azena *3 | Hotarui *4 | Urikawa *5 | Mizugayatsuri *6 | |
| Comparative example 16) | | 2700 | 4 | 4 | 5 | 4 | 1 | 1 | — |
| Composition of the present invention (Wettable powder of Example 7) | 5 | 675 | 5 | 5 | 5 | 5 | 4 | 4 | — |
| | 10 | 1350 | 5 | 5 | 5 | 5 | 4 | 4 | — |
| | 20 | 2700 | 5 | 5 | 5 | 5 | 5 | 5 | — |
| Not treated | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 6

(pre-transplanting treatment-5)

| Test agent | Dose of active ingredient g ai/ha | | Herbicidal effect | | | | | | Phytotoxicity on paddy rice |
|---|---|---|---|---|---|---|---|---|---|
| | Component A | Component B | Hie *1 | Konagi *2 | Azena *3 | Hotarui *4 | Urikawa *5 | Mizugayatsuri *6 | |
| Component A: Compound No. 1 (Wettable powder of Comparative example 24) | 5 | | 5 | 4 | 3 | 3 | 0 | 1 | — |
| | 10 | | 5 | 5 | 4 | 4 | 0 | 2 | — |
| | 20 | | 5 | 5 | 4 | 4 | 1 | 3 | — |
| Component B: MC-79 (Wettable powder of Comparative example 18) | | 500 | 2 | 2 | 2 | 1 | 0 | 0 | — |
| | | 1000 | 4 | 3 | 4 | 2 | 2 | 0 | — |
| | | 2000 | 5 | 4 | 4 | 3 | 3 | 1 | — |
| Composition of the present invention (Wettable powder of Example 9) | 5 | 500 | 5 | 5 | 5 | 5 | 4 | 4 | — |
| | 10 | 1000 | 5 | 5 | 5 | 5 | 5 | 5 | — |
| | 20 | 2000 | 5 | 5 | 5 | 5 | 5 | 5 | — |
| Not treated | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 7

(pre-transplanting treatment-6)

| Test agent | Dose of active ingredient g ai/ha | | | Herbicidal effect | | | | | | Phytotoxicity on paddy rice |
|---|---|---|---|---|---|---|---|---|---|---|
| | Component A | Component B | Component B | Hie *1 | Konagi *2 | Azena *3 | Hotarui *4 | Urikawa *5 | Mizugayatsuri *6 | |
| Component A: Compound No. 1 | 10 | | | 5 | 4 | 3 | 3 | 0 | 1 | — |
| (Flowable of Comparative | 20 | | | 5 | 5 | 4 | 4 | 0 | 2 | — |
| example 1) | 40 | | | 5 | 5 | 4 | 4 | 1 | 3 | — |
| Component B: MY-71 | | 300 | | 0 | 4 | 3 | 0 | 3 | 2 | — |
| (Flowable of Comparative | | 600 | | 0 | 4 | 4 | 2 | 4 | 3 | — |
| example 4) | | 1200 | | 1 | 5 | 5 | 5 | 5 | 4 | — |
| Component B: S-47 | | | 250 | 1 | 2 | 2 | 3 | 0 | 1 | — |
| (Flowable of Comparative | | | 500 | 2 | 3 | 3 | 3 | 0 | 3 | — |
| example 8) | | | 1000 | 4 | 5 | 3 | 5 | 2 | 5 | — |
| Composition of the present | 10 | 300 | 250 | 5 | 5 | 5 | 5 | 5 | 5 | — |
| invention | 20 | 600 | 500 | 5 | 5 | 5 | 5 | 5 | 5 | — |
| (Flowable of Example 1) | 40 | 1200 | 1000 | 5 | 5 | 5 | 5 | 5 | 5 | — |
| Not treated | | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 8

(pre-transplanting treatment-7)

| Test agent | Dose of active ingredient g ai/ha | | | Herbicidal effect | | | | | | Phytotoxicity on paddy rice |
|---|---|---|---|---|---|---|---|---|---|---|
| | Component A | Component B | Component B | Hie *1 | Konagi *2 | Azena *3 | Hotarui *4 | Urikawa *5 | Mizugayatsuri *6 | |
| Component A: Compound No. 1 | 7.5 | | | 5 | 4 | 3 | 3 | 0 | 1 | — |
| (Flowable of Comparative | 15 | | | 5 | 5 | 4 | 4 | 0 | 2 | — |
| example 1) | 30 | | | 5 | 5 | 4 | 4 | 1 | 3 | — |
| Component B: MY-71 | | 250 | | 0 | 3 | 3 | 0 | 3 | 2 | — |
| (Flowable of Comparative | | 500 | | 0 | 4 | 4 | 1 | 4 | 3 | — |
| example 4) | | 1000 | | 1 | 5 | 5 | 4 | 5 | 3 | — |
| Component B: JC-940 | | | 250 | 0 | 0 | 0 | 1 | 0 | 1 | — |
| (Flowable of Comparative | | | 500 | 2 | 1 | 0 | 3 | 0 | 3 | — |
| example 14) | | | 1000 | 4 | 2 | 1 | 5 | 2 | 5 | — |
| Composition of the present | 7.5 | 250 | 250 | 5 | 5 | 5 | 5 | 5 | 5 | — |
| invention | 15 | 500 | 500 | 5 | 5 | 5 | 5 | 5 | 5 | — |
| (Flowable of Example 13) | 30 | 1000 | 1000 | 5 | 5 | 5 | 5 | 5 | 5 | — |
| Not treated | | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 9

(pre-transplanting treatment-8)

| Test agent | Dose of active ingredient g ai/ha | | | | Herbicidal effect | | | | | | Phytotoxicity on paddy rice |
|---|---|---|---|---|---|---|---|---|---|---|---|
| | Component A | Component B | Component B | Component B | Hie *1 | Konagi *2 | Azena *3 | Hotarui *4 | Urikawa *5 | Mizugayatsuri *6 | |
| Component A: Compound No. 1 | 10 | | | | 5 | 4 | 3 | 3 | 0 | 1 | — |
| (Flowable of Comparative | 20 | | | | 5 | 5 | 4 | 4 | 0 | 2 | — |
| example 1) | 40 | | | | 5 | 5 | 4 | 4 | 1 | 3 | — |
| Component B: MY-71 | | 250 | | | 0 | 3 | 3 | 0 | 3 | 2 | — |
| (Flowable of Comparative | | 500 | | | 0 | 4 | 4 | 1 | 4 | 3 | — |
| example 4) | | 1000 | | | 1 | 5 | 5 | 4 | 5 | 3 | — |
| Component B: M-15 | | | 75 | | 1 | 2 | 1 | 3 | 3 | 0 | — |
| (Flowable of Comparative | | | 150 | | 2 | 4 | 4 | 4 | 4 | 1 | — |
| example 6) | | | 300 | | 4 | 5 | 5 | 5 | 4 | 1 | — |
| Component B: S-47 | | | | 250 | 1 | 2 | 2 | 3 | 0 | 1 | — |
| (Flowable of Comparative | | | | 500 | 2 | 3 | 3 | 3 | 0 | 3 | — |
| example 8) | | | | 1000 | 4 | 5 | 3 | 5 | 2 | 5 | — |
| Composition of the present | 10 | 250 | 75 | 250 | 5 | 5 | 5 | 5 | 5 | 5 | — |
| invention | 20 | 500 | 150 | 500 | 5 | 5 | 5 | 5 | 5 | 5 | — |
| (Flowable of Example 15) | 40 | 1000 | 300 | 1000 | 5 | 5 | 5 | 5 | 5 | 5 | — |
| Not treated | | | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 10

(pre-transplanting treatment-9)

| Test agent | Dose of active ingredient g ai/ha | | | | Herbicidal effect | | | | | | Phytotoxicity on paddy rice |
|---|---|---|---|---|---|---|---|---|---|---|---|
| | Component A | Component B | Component B | Component B | Hie *1 | Konagi *2 | Azena *3 | Hotarui *4 | Urikawa *5 | Mizugayatsuri *6 | |
| Component A: Compound No. 1 | 10 | | | | 5 | 4 | 3 | 3 | 0 | 1 | — |
| (Wettable powder of | 20 | | | | 5 | 5 | 4 | 4 | 0 | 2 | — |
| Comparative example 24) | 40 | | | | 5 | 5 | 4 | 4 | 1 | 3 | — |
| Component B: MY-71 | | 250 | | | 0 | 3 | 3 | 0 | 3 | 2 | — |
| (Wettable powder of | | 500 | | | 0 | 4 | 4 | 1 | 4 | 3 | — |
| Comparative example 20) | | 1000 | | | 1 | 5 | 5 | 4 | 5 | 3 | — |
| Component B: MY-15 | | | 75 | | 1 | 2 | 1 | 3 | 3 | 0 | — |
| (Wettable powder of | | | 150 | | 2 | 4 | 4 | 4 | 4 | 1 | — |
| Comparative example 21) | | | 300 | | 4 | 5 | 5 | 5 | 4 | 1 | — |
| Component B: NS-112 | | | | 113 | 2 | 0 | 0 | 3 | 0 | 3 | — |
| (Wettable powder of | | | | 225 | 3 | 1 | 0 | 3 | 0 | 4 | — |
| Comparative example 10) | | | | 450 | 5 | 2 | 1 | 5 | 2 | 5 | — |
| Composition of the present | 10 | 250 | 75 | 113 | 5 | 5 | 5 | 5 | 5 | 5 | — |
| invention | 20 | 500 | 150 | 225 | 5 | 5 | 5 | 5 | 5 | 5 | — |
| (Wettable powder of) Example 17) | 40 | 1000 | 300 | 450 | 5 | 5 | 5 | 5 | 5 | 5 | — |
| Not treated | | | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

Text example 2

(Early watergrass one-leaf stage treatment)

Portions of paddy field soil and portions of chemical fertilizer were put in Wagner pots having an area of 1/5,000 a, respectively, and an appropriate amount of water was added each, followed by sufficient mixing to give a sort of paddy fields. Two rice seedlings at the two-leaf stage grown in advance in a green-house were transplanted per pot with two seedlings at one hill, certain amounts of seeds of hie (*Echinochloa oryzicola* (common name: Early watergrass)), konagi (*Monochoria vaginalis*), azena (*Lindernia procumbens* (common name: Common falsepimpernel)) and hotarui (*Scirpus juncoides* (common name: Japanese bulrush)) were sown respectively per pot, certain amounts of tubers of urikawa (*Sagittaria pygmaea*) and mizugayatsuri (*Cyperus serotinus*) were planted respectively per pot, and water was poured into each pot to a water depth of 3 cm.

After the weeds of early watergrass were grown up to the one-leaf stage in a greenhouse, the formulations prepared in the above examples and comparative examples were applied thereto, respectively, so that the doses of the active ingredients became those shown in Tables 11 to 14, respectively.

Herbicidal effects on these weeds and phytotoxicity on the paddy rice were assessed 30 days after the chemical treatment in accordance with the criteria in Test example 1.

The results are shown in the following Tables 11 to 14.

TABLE 11

(Early watergrass one-leaf stage treatment-1)

| Test agent | Dose of active ingredient g ai/ha Component A | Component B | Herbicidal effect Hie *1 | Konagi *2 | Azena *3 | Hotarui *4 | Urikawa *5 | Mizugayatsuri *6 | Phytotoxicity on paddy rice |
|---|---|---|---|---|---|---|---|---|---|
| Component A: Compound No. 1 | 5 | | 5 | 2 | 2 | 2 | 0 | 1 | — |
| (Flowable of Comparative | 10 | | 5 | 3 | 3 | 3 | 0 | 2 | — |
| example 1) | 20 | | 5 | 4 | 4 | 4 | 1 | 3 | — |
| Component B: MY-71 | | 250 | 0 | 2 | 3 | 0 | 3 | 1 | — |
| (Flowable of Comparative | | 500 | 0 | 3 | 4 | 1 | 4 | 2 | — |
| example 4) | | 1000 | 1 | 4 | 4 | 4 | 5 | 3 | — |
| Composition of the present | 5 | 250 | 5 | 5 | 5 | 5 | 5 | 4 | — |
| invention | 10 | 500 | 5 | 5 | 5 | 5 | 5 | 5 | — |
| (Flowable of Example 3) | 20 | 1000 | 5 | 5 | 5 | 5 | 5 | 5 | — |
| Not treated | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 12

(Early watergrass one-leaf stage treatment-2)

| Test agent | Dose of active ingredient g ai/ha Component A | Component B | Herbicidal effect Hie *1 | Konagi *2 | Azena *3 | Hotarui *4 | Urikawa *5 | Mizugayatsuri *6 | Phytotoxicity on paddy rice |
|---|---|---|---|---|---|---|---|---|---|
| Component A: Compound No. 1 | 5 | | 5 | 2 | 2 | 2 | 0 | 1 | — |
| (Flowable of Comparative | 10 | | 5 | 3 | 3 | 3 | 0 | 2 | — |
| example 1) | 20 | | 5 | 4 | 4 | 4 | 1 | 3 | — |
| Component B: SK-23 | | 500 | 1 | 0 | 0 | 2 | 0 | 3 | — |
| (Flowable of Comparative | | 1000 | 2 | 2 | 1 | 3 | 0 | 4 | — |
| example 12) | | 2000 | 3 | 3 | 2 | 4 | 1 | 5 | — |
| Composition of the present | 5 | 500 | 5 | 5 | 5 | 5 | 3 | 5 | — |
| invention | 10 | 1000 | 5 | 5 | 5 | 5 | 4 | 5 | — |
| (Flowable of Example 5) | 20 | 2000 | 5 | 5 | 5 | 5 | 5 | 5 | — |
| Not treated | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 13

(Early watergrass one-leaf stage treatment-3)

| Test agent | Dose of active ingredient g ai/ha | | Herbicidal effect | | | | | | Phytotoxicity on paddy rice |
|---|---|---|---|---|---|---|---|---|---|
| | Component A | Component B | Hie *1 | Konagi *2 | Azena *3 | Hotarui *4 | Urikawa *5 | Mizugayatsuri *6 | |
| Component A: Compound No. 1 | 5 | | 5 | 2 | 2 | 2 | 0 | 1 | — |
| (Wettable powder of | 10 | | 5 | 3 | 3 | 3 | 0 | 2 | — |
| Comparative example 24) | 20 | | 5 | 4 | 4 | 4 | 1 | 3 | — |
| Component B: CNP | | 675 | 1 | 2 | 2 | 2 | 0 | 0 | — |
| (Wettable powder of | | 1350 | 2 | 2 | 3 | 3 | 0 | 0 | — |
| Comparative example 16) | | 2700 | 3 | 4 | 4 | 4 | 1 | 1 | — |
| Composition of the present | 5 | 675 | 5 | 5 | 5 | 5 | 4 | 4 | — |
| invention | 10 | 1350 | 5 | 5 | 5 | 5 | 4 | 4 | — |
| (Wettable powder of Example 7) | 20 | 2700 | 5 | 5 | 5 | 5 | 5 | 5 | — |
| Not treated | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 14

(Early watergrass one-leaf stage treatment-4)

| Test agent | Dose of active ingredient g ai/ha | | Herbicidal effect | | | | | | Phytotoxicity on paddy rice |
|---|---|---|---|---|---|---|---|---|---|
| | Component A | Component B | Hie *1 | Konagi *2 | Azena *3 | Hotarui *4 | Urikawa *5 | Mizugayatsuri *6 | |
| Component A: Compound No. 1 | 5 | | 5 | 2 | 2 | 2 | 0 | 1 | — |
| (Wettable powder of | 10 | | 5 | 3 | 3 | 3 | 0 | 2 | — |
| Comparative example 24) | 20 | | 5 | 4 | 4 | 4 | 1 | 3 | — |
| Component B: MC-79 | | 500 | 1 | 1 | 1 | 0 | 0 | 0 | — |
| (Wettable powder of | | 1000 | 3 | 2 | 3 | 1 | 1 | 0 | — |
| Comparative example 18) | | 2000 | 4 | 3 | 4 | 3 | 2 | 1 | — |
| Composition of the present | 5 | 500 | 5 | 5 | 5 | 5 | 4 | 4 | — |
| invention | 10 | 1000 | 5 | 5 | 5 | 5 | 4 | 4 | — |
| (Wettable powder of Example 9) | 20 | 2000 | 5 | 5 | 5 | 5 | 5 | 5 | — |
| Not treated | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

Text example 3

(Early watergrass 2.5-leaf stage treatment)

Portions of paddy field soil and portions of chemical fertilizer were put in Wagner pots having an area of 1/5,000 a, respectively, and an appropriate amount of water was added each, followed by sufficient mixing to give a sort of paddy fields. Two rice seedlings at the two-leaf stage grown in advance in a greenhouse were transplanted per pot with two seedlings at one hill, certain amounts of seeds of hie (*Echinochloa oryzicola* (common name: Early watergrass)), konagi (*Monochoria vaginalis*), azena (*Lindernia procumbens* (common name: Common falsepimpernel)) and hotarui (*Scirpus juncoides* (common name: Japanese bulrush)) were sown respectively per pot, certain amounts of tubers of urikawa (*Sagittaria pygmaea*) and mizugayatsuri (*Cyperus serotinus*) were planted respectively per pot, and water was poured into each pot to a water depth of 3 cm.

After the weeds of early watergrass were grown up to the 2.5-leaf stage in a greenhouse, the formulations prepared in the above examples and comparative examples were applied thereto, respectively, so that the doses of the active ingredients became those shown in Tables 15 to 20, respectively.

Herbicidal effects on these weeds and phytotoxicity on the paddy rice were assessed 30 days after the chemical treatment in accordance with the criteria in Test example 1.

The results are shown in the following Tables 15 to 20.

TABLE 15

(Early watergrass 2.5-leaf stage treatment-1)

| Test agent | Dose of active ingredient g ai/ha | | | Herbicidal effect | | | | | | Phytotoxicity on paddy rice |
|---|---|---|---|---|---|---|---|---|---|---|
| | Component A | Component B | Component B | Hie *1 | Konagi *2 | Azena *3 | Hotarui *4 | Urikawa *5 | Mizugayatsuri *6 | |
| Component A: Compound No. 1 | 10 | | | 3 | 0 | 0 | 0 | 0 | 1 | — |
| (Flowable of Comparative | 20 | | | 4 | 1 | 0 | 1 | 0 | 1 | — |
| example 1) | 40 | | | 5 | 2 | 1 | 2 | 1 | 3 | — |
| Component B: MY-71 | | 300 | | 0 | 1 | 1 | 0 | 2 | 1 | — |
| (Flowable of Comparative | | 600 | | 0 | 3 | 3 | 2 | 3 | 1 | — |
| example 4) | | 1200 | | 1 | 4 | 4 | 3 | 4 | 3 | — |
| Component B: S-47 | | | 250 | 0 | 1 | 1 | 1 | 0 | 1 | — |
| (Flowable of Comparative | | | 500 | 0 | 2 | 2 | 2 | 0 | 2 | — |
| example 6) | | | 1000 | 1 | 4 | 2 | 4 | 2 | 3 | — |
| Composition of the present | 10 | 300 | 250 | 5 | 5 | 5 | 5 | 4 | 4 | — |
| invention | 20 | 600 | 500 | 5 | 5 | 5 | 5 | 5 | 4 | — |
| (Flowable of Example 11) | 40 | 1200 | 1000 | 5 | 5 | 5 | 5 | 5 | 5 | — |
| Not treated | | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 16

(Early watergrass 2.5-leaf stage treatment-2)

| Test agent | Dose of active ingredient g ai/ha | | | Herbicidal effect | | | | | | Phytotoxicity on paddy rice |
|---|---|---|---|---|---|---|---|---|---|---|
| | Component A | Component B | Component B | Hie *1 | Konagi *2 | Azena *3 | Hotarui *4 | Urikawa *5 | Mizugayatsuri *6 | |
| Component A: Compound No. 1 | 7.5 | | | 3 | 0 | 0 | 0 | 0 | 1 | — |
| (Flowable of Comparative | 15 | | | 4 | 1 | 0 | 1 | 0 | 1 | — |
| example 1) | 30 | | | 5 | 2 | 1 | 2 | 1 | 3 | — |
| Component B: MY-71 | | 250 | | 0 | 1 | 1 | 0 | 2 | 1 | — |
| (Flowable of Comparative | | 500 | | 0 | 3 | 3 | 2 | 3 | 1 | — |
| example 4) | | 1000 | | 1 | 4 | 4 | 3 | 4 | 3 | — |
| Component B: JC-940 | | | 250 | 0 | 0 | 0 | 1 | 0 | 1 | — |
| (Flowable of Comparative | | | 500 | 1 | 0 | 0 | 3 | 0 | 3 | — |
| example 14) | | | 1000 | 2 | 1 | 1 | 4 | 1 | 5 | — |
| Composition of the present | 7.5 | 250 | 250 | 5 | 5 | 5 | 5 | 4 | 4 | — |
| invention | 15 | 500 | 500 | 5 | 5 | 5 | 5 | 5 | 5 | — |
| (Flowable of Example 13) | 30 | 1200 | 1000 | 5 | 5 | 5 | 5 | 5 | 5 | — |
| Not treated | | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 17

(Early watergrass 2.5-leaf stage treatment-3)

| Test agent | Dose of active ingredient g ai/ha | | | | Herbicidal effect | | | | | | Phytotoxicity on paddy rice |
|---|---|---|---|---|---|---|---|---|---|---|---|
| | Component A | Component B | Component B | Component B | Hie *1 | Konagi *2 | Azena *3 | Hotarui *4 | Urikawa *5 | Mizugayatsuri *6 | |
| Component A: Compound No. 1 | 10 | | | | 3 | 0 | 0 | 0 | 0 | 1 | — |
| (Flowable of Comparative | 20 | | | | 4 | 1 | 0 | 1 | 0 | 1 | — |
| example 1) | 40 | | | | 5 | 2 | 1 | 2 | 1 | 3 | — |
| Component B: MY-71 | | 250 | | | 0 | 1 | 1 | 0 | 2 | 1 | — |
| (Flowable of Comparative | | 500 | | | 0 | 3 | 3 | 2 | 3 | 1 | — |
| example 4) | | 1000 | | | 1 | 4 | 4 | 3 | 4 | 3 | — |
| Component B: MY-15 | | | 75 | | 0 | 1 | 1 | 2 | 2 | 0 | — |
| (Flowable of Comparative | | | 150 | | 1 | 3 | 4 | 3 | 3 | 1 | — |
| example 6) | | | 300 | | 1 | 4 | 4 | 4 | 4 | 1 | — |
| Component B: S-47 | | | | 250 | 0 | 1 | 1 | 1 | 0 | 1 | — |
| (Flowable of Comparative | | | | 500 | 0 | 2 | 2 | 2 | 0 | 2 | — |
| example 8) | | | | 1000 | 1 | 4 | 2 | 4 | 2 | 3 | — |
| Composition of the present | 10 | 250 | 75 | 250 | 5 | 5 | 5 | 5 | 5 | 4 | — |
| invention | 20 | 500 | 150 | 500 | 5 | 5 | 5 | 5 | 5 | 4 | — |
| (Flowable of Example 15) | 40 | 1000 | 300 | 1000 | 5 | 5 | 5 | 5 | 5 | 5 | — |
| Not treated | | | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 18

(Early watergrass 2.5-leaf stage treatment-4)

| Test agent | Dose of active ingredient g ai/ha | | | | Herbicidal effect | | | | | | Phytotoxicity on paddy rice |
|---|---|---|---|---|---|---|---|---|---|---|---|
| | Component A | Component B | Component B | Component B | Hie *1 | Konagi *2 | Azena *3 | Hotarui *4 | Urikawa *5 | Mizugayatsuri *6 | |
| Component A: Compound No. 1 | 10 | | | | 3 | 0 | 0 | 0 | 0 | 1 | — |
| (Wettable powder of | 20 | | | | 4 | 1 | 0 | 1 | 0 | 1 | — |
| Comparative example 24) | 40 | | | | 5 | 2 | 1 | 2 | 1 | 3 | — |
| Component B: MY-71 | | 250 | | | 0 | 3 | 3 | 0 | 2 | 1 | — |
| (Wettable powder of | | 500 | | | 0 | 4 | 4 | 2 | 3 | 2 | — |
| Comparative example 20) | | 1000 | | | 1 | 4 | 4 | 4 | 5 | 3 | — |
| Component B: MY-15 | | | 75 | | 0 | 1 | 1 | 2 | 2 | 0 | — |
| (Wettable powder of | | | 150 | | 1 | 3 | 4 | 3 | 3 | 0 | — |
| Comparative example 21) | | | 300 | | 1 | 4 | 4 | 4 | 4 | 1 | — |
| Component B: NS-112 | | | | 113 | 1 | 0 | 0 | 2 | 0 | 3 | — |
| (Wettable powder of | | | | 225 | 2 | 0 | 0 | 3 | 0 | 4 | — |
| Comparative example 10) | | | | 450 | 3 | 1 | 1 | 4 | 1 | 5 | — |
| Composition of the present | 10 | 250 | 75 | 113 | 5 | 5 | 5 | 5 | 4 | 5 | — |
| invention | 20 | 500 | 150 | 225 | 5 | 5 | 5 | 5 | 5 | 5 | — |
| (Wettable powder of) Example 17) | 40 | 1000 | 300 | 450 | 5 | 5 | 5 | 5 | 5 | 5 | — |
| Not treated | | | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 19

(Early watergrass 2.5-leaf stage treatment-5)

| Test agent | Dose of active ingredient g ai/ha Component A | Component B | Herbicidal effect Hie *1 | Konagi *2 | Azena *3 | Hotarui *4 | Urikawa *5 | Mizugayatsuri *6 | Phytotoxicity on paddy rice |
|---|---|---|---|---|---|---|---|---|---|
| Component A: Compound No. 1 | 10 | | 5 | 4 | 3 | 3 | 0 | 1 | — |
| (Granule of Comparative | 20 | | 5 | 5 | 4 | 4 | 0 | 2 | — |
| example 2) | 40 | | 5 | 5 | 4 | 4 | 1 | 3 | — |
| Component B: G32911 | | 112.5 | 2 | 2 | 2 | 0 | 0 | 0 | — |
| (Granule of Comparative | | 225 | 4 | 3 | 3 | 1 | 1 | 0 | — |
| example 26) | | 450 | 5 | 5 | 5 | 3 | 3 | 1 | — |
| Composition of the present | 10 | 112.5 | 5 | 5 | 5 | 5 | 4 | 4 | — |
| invention | 20 | 225 | 5 | 5 | 5 | 5 | 5 | 5 | — |
| (Granule of Example 20) | 40 | 450 | 5 | 5 | 5 | 5 | 5 | 5 | — |
| Not treated | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 20

(Early watergrass 2.5-leaf stage treatment-6)

| Test agent | Dose of active ingredient g ai/ha Component A | Component B | Herbicidal effect Hie *1 | Konagi *2 | Azena *3 | Hotarui *4 | Urikawa *5 | Mizugayatsuri *6 | Phytotoxicity on paddy rice |
|---|---|---|---|---|---|---|---|---|---|
| Component A: Compound No. 1 | 10 | | 5 | 4 | 3 | 3 | 0 | 1 | — |
| (Granule of Comparative | 20 | | 5 | 5 | 4 | 4 | 0 | 2 | — |
| example 2) | 40 | | 5 | 5 | 4 | 4 | 1 | 3 | — |
| Component B: CG-7103 | | 82.5 | 1 | 1 | 1 | 0 | 0 | 0 | — |
| (Granule of Comparative | | 165 | 2 | 2 | 2 | 0 | 0 | 0 | — |
| example 28) | | 330 | 2 | 3 | 3 | 3 | 3 | 1 | — |
| Composition of the present | 10 | 82.5 | 5 | 5 | 5 | 5 | 4 | 4 | — |
| invention | 20 | 165 | 5 | 5 | 5 | 5 | 5 | 5 | — |
| (Granule of Example 22) | 40 | 330 | 5 | 5 | 5 | 5 | 5 | 5 | — |
| Not treated | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

Text example 4
(foliar treatment in paddy fields)

Portions of paddy field soil and portions of chemical fertilizer were put in Wagner pots having an area of 1/5,000 a, respectively, and an appropriate amount of water was added each, followed by sufficient mixing to give a sort of paddy fields. Two rice seedlings at the two-leaf stage grown in advance in a greenhouse were transplanted per pot with two seedlings at one hill, certain amounts of seeds of hie (*Echinochloa oryzicola* (common name: Early watergrass)), konagi (*Monochoria vaginalis*), azena (*Lindernia procumbens* (common name: Common falsepimpernel)) and hotarui (*Scirpus juncoides* (common name: Japanese bulrush)) were sown respectively per pot, certain amounts of tubers of urikawa (*Sagittaria pygmaea*) and mizugayatsuri (*Cyperus serotinus*) were planted respectively per pot, and water was poured into each pot to a water depth of 3 cm.

After the weeds of early watergrass were grown up to the 2.5-leaf stage in a greenhouse, the formulations prepared in the above examples and comparative examples were applied thereto, respectively, so that the doses of the active ingredients became those shown in Tables 21 to 24, respectively.

Herbicidal effects on these weeds and phytotoxicity on the paddy rice were assessed 30 days after the chemical treatment in accordance with the criteria in Test example 1.

The results are shown in the following Tables 21 to 24.

It is apparent from the above test results that the herbicidal compositions of the present invention can control various weeds at lower doses of active ingredients compared with cases in which the respective active ingredients were used alone, respectively.

TABLE 21

(foliar treatment in paddy fields-1)

| Test agent | Dose of active ingredient g ai/ha Component A | Component B | Component B | Herbicidal effect Hie *1 | Konagi *2 | Azena *3 | Hotarui *4 | Urikawa *5 | Mizugayatsuri *6 | Phytotoxicity on paddy rice |
|---|---|---|---|---|---|---|---|---|---|---|
| Component A: Compound No. 1 | 15 | | | 4 | 0 | 0 | 0 | 0 | 0 | — |
| (Granule of Comparative | 30 | | | 5 | 1 | 2 | 1 | 0 | 0 | — |
| example 29) | 60 | | | 5 | 3 | 3 | 1 | 1 | 2 | — |
| Component B: TH-913 | | 22.5 | | 0 | 3 | 3 | 2 | 4 | 4 | — |
| (Granule of Comparative | | 45 | | 1 | 5 | 5 | 3 | 4 | 4 | — |
| example 30) | | 90 | | 1 | 5 | 5 | 4 | 5 | 5 | — |
| Component B: SK-23 | | | 375 | 0 | 0 | 0 | 0 | 0 | 0 | — |
| (Granule of Comparative | | | 750 | 0 | 0 | 0 | 0 | 0 | 0 | — |
| example 31) | | | 1500 | 0 | 1 | 2 | 3 | 0 | 0 | — |
| Composition of the present | 15 | 22.5 | | 5 | 5 | 5 | 3 | 5 | 5 | — |
| invention | 30 | 45 | | 5 | 5 | 5 | 4 | 5 | 5 | — |
| (Granule of Example 23) | 60 | 90 | | 5 | 5 | 5 | 5 | 5 | 5 | — |
| Composition of the present | 15 | 22.5 | 375 | 5 | 5 | 5 | 5 | 5 | 5 | — |
| invention | 30 | 45 | 750 | 5 | 5 | 5 | 5 | 5 | 5 | — |
| (Granule of Example 24) | 60 | 90 | 1500 | 5 | 5 | 5 | 5 | 5 | 5 | — |
| Component A: Compound No. 1 | 10 | | | 4 | 0 | 0 | 0 | 0 | 0 | — |
| (Flowable of Comparative | 20 | | | 5 | 1 | 1 | 0 | 0 | 0 | — |
| example 32) | 40 | | | 5 | 3 | 3 | 2 | 2 | 2 | — |
| Component B: TH-913 | | 22.5 | | 0 | 3 | 3 | 2 | 3 | 3 | — |
| (Flowable of Comparative | | 45 | | 0 | 4 | 5 | 2 | 4 | 4 | — |
| example 33) | | 90 | | 1 | 5 | 5 | 4 | 5 | 5 | — |
| Component B: SK-23 | | | 375 | 0 | 0 | 0 | 0 | 0 | 0 | — |
| (Flowable of Comparative | | | 750 | 0 | 0 | 1 | 3 | 0 | 1 | — |
| example 34) | | | 1500 | 1 | 1 | 2 | 4 | 1 | 1 | — |
| Composition of the present | 10 | 22.5 | | 5 | 5 | 4 | 2 | 5 | 5 | — |
| invention | 20 | 45 | | 5 | 5 | 5 | 4 | 5 | 5 | — |
| (Flowable of Example 25) | 40 | 90 | | 5 | 5 | 5 | 5 | 5 | 5 | — |
| Composition of the present | 10 | 22.5 | 375 | 5 | 5 | 5 | 5 | 5 | 5 | — |
| invention | 20 | 45 | 750 | 5 | 5 | 5 | 5 | 5 | 5 | — |
| (Flowable of Example 26) | 40 | 90 | 1500 | 5 | 5 | 5 | 5 | 5 | 5 | — |
| Not treated | | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 22

(foliar treatment in paddy fields-2)

| Test agent | Dose of active ingredient g ai/ha Component A | Component B | Component B | Herbicidal effect Hie *1 | Konagi *2 | Azena *3 | Hotarui *4 | Urikawa *5 | Mizugayatsuri *6 | Phytotoxicity on paddy rice |
|---|---|---|---|---|---|---|---|---|---|---|
| Component A: Compound No. 1 | 15 | | | 4 | 0 | 0 | 0 | 0 | 0 | — |
| (Granule of Comparative | 30 | | | 5 | 1 | 2 | 1 | 0 | 0 | — |
| example 35) | 60 | | | 5 | 3 | 3 | 1 | 1 | 2 | — |
| Component B: DPX-84 | | 12.5 | | 0 | 3 | 3 | 3 | 4 | 4 | — |
| (Granule of Comparative | | 25 | | 0 | 5 | 5 | 4 | 4 | 5 | — |
| example 36) | | 50 | | 1 | 5 | 5 | 5 | 5 | 5 | — |
| Component B: SK-23 | | | 112.5 | 0 | 0 | 0 | 0 | 0 | 0 | — |
| (Granule of Comparative | | | 225 | 0 | 0 | 0 | 0 | 0 | 0 | — |
| example 37) | | | 450 | 0 | 1 | 2 | 3 | 0 | 0 | — |

TABLE 22-continued (foliar treatment in paddy fields-2)

| Test agent | Dose of active ingredient g ai/ha | | | Herbicidal effect | | | | | | Phytotoxicity on paddy rice |
|---|---|---|---|---|---|---|---|---|---|---|
| | Component A | Component B | Component B | Hie *1 | Konagi *2 | Azena *3 | Hotarui *4 | Urikawa *5 | Mizugayatsuri *6 | |
| Composition of the present | 15 | 12.5 | | 5 | 5 | 5 | 4 | 5 | 5 | — |
| invention | 30 | 25 | | 5 | 5 | 5 | 5 | 5 | 5 | — |
| (Granule of Example 29) | 60 | 50 | | 5 | 5 | 5 | 5 | 5 | 5 | — |
| Composition of the present | 15 | 12.5 | 112.5 | 5 | 5 | 5 | 5 | 5 | 5 | — |
| invention | 30 | 25 | 225 | 5 | 5 | 5 | 5 | 5 | 5 | — |
| (Granule of Example 30) | 60 | 50 | 450 | 5 | 5 | 5 | 5 | 5 | 5 | — |
| Component A: Compound No. 1 | 10 | | | 5 | 0 | 0 | 0 | 0 | 0 | — |
| (Flowable of Comparative | 20 | | | 5 | 1 | 1 | 0 | 0 | 0 | — |
| example 38) | 40 | | | 5 | 3 | 3 | 2 | 2 | 2 | — |
| Component B: DPX-84 | | 12.5 | | 0 | 3 | 3 | 2 | 2 | 3 | — |
| (Flowable of Comparative | | 25 | | 0 | 3 | 4 | 3 | 3 | 4 | — |
| example 39) | | 50 | | 1 | 5 | 5 | 5 | 5 | 5 | — |
| Component B: SK-23 | | | 112.5 | 0 | 0 | 0 | 0 | 0 | 0 | — |
| (Flowable of Comparative | | | 225 | 0 | 0 | 1 | 3 | 0 | 1 | — |
| example 40) | | | 450 | 1 | 1 | 2 | 4 | 1 | 1 | — |
| Composition of the present | 10 | 12.5 | | 5 | 5 | 4 | 4 | 5 | 5 | — |
| invention | 20 | 25 | | 5 | 5 | 5 | 5 | 5 | 5 | — |
| (Flowable of Example 31) | 40 | 50 | | 5 | 5 | 5 | 5 | 5 | 5 | — |
| Composition of the present | 10 | 12.5 | 112.5 | 5 | 5 | 5 | 5 | 5 | 5 | — |
| invention | 20 | 25 | 225 | 5 | 5 | 5 | 5 | 5 | 5 | — |
| (Flowable of Example 32) | 40 | 50 | 450 | 5 | 5 | 5 | 5 | 5 | 5 | — |
| Not treated | | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 23

(foliar treatment in paddy fields-3)

| Test agent | Dose of active ingredient g ai/ha | | | Herbicidal effect | | | | | | Phytotoxicity on paddy rice |
|---|---|---|---|---|---|---|---|---|---|---|
| | Component A | Component B | Component B | Hie *1 | Konagi *2 | Azena *3 | Hotarui *4 | Urikawa *5 | Mizugayatsuri *6 | |
| Component A: Compound No. 1 | 15 | | | 4 | 0 | 0 | 0 | 0 | 0 | — |
| (Granule of Comparative | 30 | | | 5 | 1 | 2 | 1 | 0 | 0 | — |
| example 35) | 60 | | | 5 | 3 | 3 | 1 | 1 | 2 | — |
| Component B: NC-311 | | 5 | | 0 | 3 | 4 | 2 | 4 | 4 | — |
| (Granule of Comparative | | 10 | | 1 | 5 | 5 | 5 | 4 | 4 | — |
| example 41) | | 20 | | 3 | 5 | 5 | 5 | 5 | 5 | — |
| Component B: SK-23 | | | 112.5 | 0 | 0 | 0 | 0 | 0 | 0 | — |
| (Granule of Comparative | | | 225 | 0 | 0 | 0 | 0 | 0 | 0 | — |
| example 37) | | | 450 | 0 | 1 | 2 | 3 | 0 | 0 | — |
| Composition of the present | 15 | 5 | | 5 | 5 | 5 | 5 | 4 | 5 | — |
| invention | 30 | 10 | | 5 | 5 | 5 | 5 | 5 | 5 | — |
| (Granule of Example 35) | 60 | 20 | | 5 | 5 | 5 | 5 | 5 | 5 | — |
| Composition of the present | 15 | 5 | 112.5 | 5 | 5 | 5 | 5 | 5 | 5 | — |
| invention | 30 | 10 | 225 | 5 | 5 | 5 | 5 | 5 | 5 | — |
| (Granule of Example 36) | 60 | 20 | 450 | 5 | 5 | 5 | 5 | 5 | 5 | — |
| Component A: Compound No. 1 | 10 | | | 4 | 0 | 0 | 0 | 0 | 0 | — |
| (Flowable of Comparative | 20 | | | 5 | 1 | 1 | 0 | 0 | 0 | — |
| example 38) | 40 | | | 5 | 3 | 3 | 2 | 2 | 2 | — |
| Component B: NC-311 | | 5 | | 0 | 3 | 3 | 4 | 4 | 3 | — |
| (Flowable of Comparative | | 10 | | 0 | 4 | 5 | 5 | 5 | 5 | — |
| example 42) | | 20 | | 1 | 5 | 5 | 5 | 5 | 5 | — |
| Component B: SK-23 | | | 112.5 | 0 | 0 | 0 | 0 | 0 | 0 | — |

TABLE 23-continued (foliar treatment in paddy fields-3)

| Test agent | Dose of active ingredient g ai/ha | | | Herbicidal effect | | | | | | Phytotoxicity on paddy rice |
|---|---|---|---|---|---|---|---|---|---|---|
| | Component A | Component B | Component B | Hie *1 | Konagi *2 | Azena *3 | Hotarui *4 | Urikawa *5 | Mizugayatsuri *6 | |
| (Flowable of Comparative example 40) | | | 225 | 0 | 0 | 1 | 3 | 0 | 1 | — |
| | | | 450 | 1 | 1 | 2 | 4 | 1 | 1 | — |
| Composition of the present invention (Flowable of Example 37) | 10 | 5 | | 5 | 5 | 4 | 5 | 5 | 5 | — |
| | 20 | 10 | | 5 | 5 | 5 | 5 | 5 | 5 | — |
| | 40 | 20 | | 5 | 5 | 5 | 5 | 5 | 5 | — |
| Composition of the present invention (Flowable of Example 38) | 10 | 5 | 112.5 | 5 | 5 | 5 | 4 | 5 | 5 | — |
| | 20 | 10 | 225 | 5 | 5 | 5 | 5 | 5 | 5 | — |
| | 40 | 20 | 450 | 5 | 5 | 5 | 5 | 5 | 5 | — |
| Not treated | | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 24

(foliar treatment in paddy fields-4)

| Test agent | Dose of active ingredient g ai/ha | | | | Herbicidal effect | | | | | | Phytotoxicity on paddy rice |
|---|---|---|---|---|---|---|---|---|---|---|---|
| | Component A | Component B | Component B | Component B | Hie *1 | Konagi *2 | Azena *3 | Hotarui *4 | Urikawa *5 | Mizugayatsuri *6 | |
| Component A: Compound No. 1 (Granule of Comparative example 29) | 15 | | | | 4 | 0 | 0 | 0 | 0 | 0 | — |
| | 30 | | | | 5 | 1 | 2 | 1 | 0 | 0 | — |
| | 60 | | | | 5 | 3 | 3 | 1 | 1 | 2 | — |
| Component B: DPX-84 (Granule of Comparative example 43) | | 7.5 | | | 0 | 2 | 2 | 3 | 3 | 3 | — |
| | | 15 | | | 0 | 3 | 3 | 3 | 3 | 3 | — |
| | | 30 | | | 1 | 4 | 5 | 4 | 4 | 4 | — |
| Component B: DPX-47 (Granule of Comparative example 44) | | | 1.5 | | 0 | 2 | 2 | 3 | 4 | 4 | — |
| | | | 3 | | 0 | 3 | 3 | 4 | 4 | 5 | — |
| | | | 6 | | 1 | 4 | 3 | 5 | 5 | 5 | — |
| Component B: SK-23 (Granule of Comparative example 45) | | | | 113 | 0 | 0 | 0 | 0 | 0 | 0 | — |
| | | | | 225 | 0 | 0 | 0 | 0 | 0 | 0 | — |
| | | | | 450 | 0 | 1 | 2 | 3 | 0 | 0 | — |
| Composition of the present invention (Granule of Example 41) | 15 | 7.5 | 1.5 | | 5 | 5 | 5 | 4 | 5 | 5 | — |
| | 30 | 15 | 3 | | 5 | 5 | 5 | 5 | 5 | 5 | — |
| | 60 | 30 | 6 | | 5 | 5 | 5 | 5 | 5 | 5 | — |
| Composition of the present invention (Granule of Example 42) | 15 | 7.5 | 1.5 | 113 | 5 | 5 | 5 | 5 | 5 | 5 | — |
| | 30 | 15 | 3 | 225 | 5 | 5 | 5 | 5 | 5 | 5 | — |
| | 60 | 30 | 6 | 450 | 5 | 5 | 5 | 5 | 5 | 5 | — |
| Component A: Compound No. 1 (Flowable of Comparative example 46) | 10 | | | | 4 | 0 | 0 | 0 | 0 | 0 | — |
| | 20 | | | | 5 | 1 | 1 | 0 | 0 | 0 | — |
| | 40 | | | | 5 | 3 | 3 | 2 | 2 | 2 | — |
| Component B: DPX-84 (Flowable of Comparative example 47) | | 7.5 | | | 0 | 3 | 2 | 3 | 3 | 3 | — |
| | | 15 | | | 0 | 3 | 4 | 3 | 3 | 4 | — |
| | | 30 | | | 1 | 5 | 5 | 4 | 4 | 4 | — |
| Component B: DPX-47 (Flowable of Comparative example 48) | | | 1.5 | | 0 | 2 | 2 | 3 | 4 | 4 | — |
| | | | 3 | | 0 | 3 | 3 | 4 | 5 | 5 | — |
| | | | 6 | | 1 | 4 | 3 | 5 | 5 | 5 | — |
| Component B: SK-23 (Flowable of Comparative example 49) | | | | 113 | 0 | 0 | 0 | 0 | 0 | 0 | — |
| | | | | 225 | 0 | 0 | 1 | 3 | 0 | 1 | — |
| | | | | 450 | 1 | 1 | 2 | 4 | 1 | 1 | — |
| Composition of the present invention (Flowable of Example 43) | 10 | 7.5 | 1.5 | | 5 | 5 | 4 | 4 | 5 | 5 | — |
| | 20 | 15 | 3 | | 5 | 5 | 5 | 5 | 5 | 5 | — |
| | 40 | 30 | 6 | | 5 | 5 | 5 | 5 | 5 | 5 | — |
| Composition of the present | 10 | 7.5 | 1.5 | 113 | 5 | 5 | 5 | 5 | 5 | 5 | — |

TABLE 24-continued (foliar treatment in paddy fields-4)

| Test agent | Dose of active ingredient g ai/ha | | | | Herbicidal effect | | | | | | Phytotoxicity on paddy rice |
|---|---|---|---|---|---|---|---|---|---|---|---|
| | Component A | Component B | Component B | Component B | Hie *1 | Konagi *2 | Azena *3 | Hotarui *4 | Urikawa *5 | Mizugayatsuri *6 | |
| invention | 20 | 15 | 3 | 225 | 5 | 5 | 5 | 5 | 5 | 5 | — |
| (Flowable of Example 44) | 40 | 30 | 6 | 450 | 5 | 5 | 5 | 5 | 5 | 5 | — |
| Not treated | | | | | 0 | 0 | 0 | 0 | 0 | 0 | — |

Note:
*1 Hie: *Echinochloa oryzicola* (common name: Early watergrass)
*2 Konagi: Monochoria vaginalis
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

Text example 5

(field test)

A paddy field where rice seedlings had been transplanted according to a usual farming method was divided by using plastic sheets (product of Shin-Etsu Chemical Co., Ltd.; trade name: "Azenami") so that the surface area of each portion became 10 m² (4××2.5 m). The weeds of early watergrass were grown up to the 2.5-leaf stage, and the formulations prepared in the above examples and comparative examples were applied thereto, respectively, so that the doses of the active ingredients became those shown in Tables 25 to 28.

Thereafter, usual field maintenance was made, and herbicidal effects on these weeds and phytotoxicity on the paddy rice were assessed 30 days after the chemical treatment in accordance with the criteria in Test example 1.

The results are shown in the following Tables 25 to 28.

TABLE 25

(field test-1)

| Test agent | Dose of active ingredient g ai/ha | | | Herbicidal effect | | | | | | Phytotoxicity on paddy rice |
|---|---|---|---|---|---|---|---|---|---|---|
| | Component A | Component B | Component B | Hie *1 | Konagi *2 | Azena *3 | Hotarui *4 | Urikawa *5 | Mizugayatsuri *6 | |
| Component A: Compound No. 1 | 15 | | | 4 | 0 | 0 | 0 | 0 | 0 | — |
| (Granule of Comparative | 30 | | | 4 | 1 | 1 | 0 | 0 | 0 | — |
| example 29) | 60 | | | 5 | 2 | 1 | 1 | 2 | 2 | — |
| Component B: TH-913 | | 22.5 | | 0 | 3 | 3 | 2 | 3 | 4 | — |
| (Granule of Comparative | | 45 | | 0 | 4 | 4 | 3 | 4 | 4 | — |
| example 30) | | 90 | | 1 | 5 | 5 | 4 | 5 | 5 | — |
| Component B: SK-23 | | | 375 | 0 | 0 | 0 | 0 | 0 | 0 | — |
| (Granule of Comparative | | | 750 | 0 | 0 | 0 | 1 | 0 | 0 | — |
| example 31) | | | 1500 | 0 | 1 | 1 | 2 | 1 | 1 | — |
| Composition of the present | 15 | 22.5 | | 4 | 3 | 4 | 2 | 3 | 4 | — |
| invention | 30 | 45 | | 5 | 4 | 5 | 4 | 4 | 4 | — |
| (Granule of Example 23) | 60 | 90 | | 5 | 5 | 5 | 5 | 5 | 5 | — |
| Composition of the present | 15 | 22.5 | 375 | 5 | 5 | 5 | 5 | 5 | 5 | — |
| invention | 30 | 45 | 750 | 5 | 5 | 5 | 5 | 5 | 5 | — |
| (Granule of Example 24) | 60 | 90 | 1500 | 5 | 5 | 5 | 5 | 5 | 5 | — |
| Component A: Compound No. 1 | 10 | | | 4 | 0 | 0 | 0 | 0 | 0 | — |
| (Flowable of Comparative | 20 | | | 5 | 1 | 0 | 0 | 0 | 0 | — |
| example 26) | 40 | | | 5 | 3 | 1 | 1 | 1 | 2 | — |
| Component B: TH-913 | | 22.5 | | 0 | 3 | 3 | 2 | 3 | 3 | — |
| (Flowable of Comparative | | 45 | | 0 | 4 | 4 | 2 | 4 | 4 | — |
| example 27) | | 90 | | 1 | 5 | 5 | 4 | 5 | 5 | — |
| Component B: SK-23 | | | 375 | 0 | 0 | 0 | 0 | 0 | 0 | — |
| (Flowable of Comparative | | | 750 | 0 | 0 | 0 | 2 | 0 | 0 | — |
| example 28) | | | 1500 | 0 | 1 | 1 | 3 | 1 | 1 | — |
| Composition of the present | 10 | 22.5 | | 5 | 4 | 4 | 2 | 4 | 4 | — |
| invention | 20 | 45 | | 5 | 5 | 4 | 3 | 4 | 4 | — |

TABLE 25-continued (field test-1)

| Test agent | Dose of active ingredient g ai/ha | | | Herbicidal effect | | | | | | Phytotoxicity on paddy rice |
|---|---|---|---|---|---|---|---|---|---|---|
| | Component A | Component B | Component B | Hie *1 | Konagi *2 | Azena *3 | Hotarui *4 | Urikawa *5 | Mizugayatsuri *6 | |
| (Flowable of Example 25) | 40 | 90 | | 5 | 5 | 5 | 5 | 5 | 5 | — |
| Composition of the present | 10 | 22.5 | 375 | 5 | 5 | 5 | 5 | 5 | 5 | — |
| invention | 20 | 45 | 750 | 5 | 5 | 5 | 5 | 5 | 5 | — |
| (Flowable of Example 26) | 40 | 90 | 1500 | 5 | 5 | 5 | 5 | 5 | 5 | — |
| Not treated | | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 26

(field test-2)

| Test agent | Dose of active ingredient g ai/ha | | | Herbicidal effect | | | | | | Phytotoxicity on paddy rice |
|---|---|---|---|---|---|---|---|---|---|---|
| | Component A | Component B | Component B | Hie *1 | Konagi *2 | Azena *3 | Hotarui *4 | Urikawa *5 | Mizugayatsuri *6 | |
| Component A: Compound No. 1 | 15 | | | 4 | 0 | 0 | 0 | 0 | 0 | — |
| (Granule of Comparative | 30 | | | 4 | 1 | 1 | 0 | 0 | 0 | — |
| example 35) | 60 | | | 5 | 2 | 1 | 1 | 2 | 2 | — |
| Component B: DPX-84 | | 12.5 | | 0 | 3 | 3 | 2 | 3 | 3 | — |
| (Granule of Comparative | | 25 | | 0 | 4 | 4 | 3 | 4 | 4 | — |
| example 36) | | 50 | | 1 | 5 | 5 | 4 | 5 | 5 | — |
| Component B: SK-23 | | | 112.5 | 0 | 0 | 0 | 0 | 0 | 0 | — |
| (Granule of Comparative | | | 225 | 0 | 0 | 0 | 1 | 0 | 0 | — |
| example 37) | | | 450 | 0 | 1 | 1 | 2 | 1 | 1 | — |
| Composition of the present | 15 | 12.5 | | 5 | 5 | 3 | 3 | 4 | 4 | — |
| invention | 30 | 25 | | 5 | 5 | 5 | 5 | 5 | 5 | — |
| (Granule of Example 29) | 60 | 50 | | 5 | 5 | 5 | 5 | 5 | 5 | — |
| Composition of the present | 15 | 12.5 | 112.5 | 5 | 5 | 5 | 5 | 5 | 5 | — |
| invention | 30 | 25 | 225 | 5 | 5 | 5 | 5 | 5 | 5 | — |
| (Granule of Example 30) | 60 | 50 | 450 | 5 | 5 | 5 | 5 | 5 | 5 | — |
| Component A: Compound No. 1 | 10 | | | 4 | 0 | 0 | 0 | 0 | 0 | — |
| (Flowable of Comparative | 20 | | | 5 | 1 | 0 | 0 | 0 | 0 | — |
| example 38) | 40 | | | 5 | 3 | 1 | 1 | 1 | 2 | — |
| Component B: DPX-84 | | 12.5 | | 0 | 3 | 3 | 2 | 2 | 3 | — |
| (Flowable of Comparative | | 45 | | 0 | 4 | 4 | 2 | 4 | 4 | — |
| example 39) | | 50 | | 1 | 5 | 5 | 4 | 5 | 5 | — |
| Component B: SK-23 | | | 112.5 | 0 | 0 | 0 | 0 | 0 | 0 | — |
| (Flowable of Comparative | | | 225 | 0 | 0 | 0 | 2 | 0 | 0 | — |
| example 40) | | | 450 | 0 | 1 | 1 | 3 | 0 | 1 | — |
| Composition of the present | 10 | 12.5 | | 5 | 5 | 4 | 3 | 5 | 4 | — |
| invention | 20 | 25 | | 5 | 5 | 5 | 5 | 5 | 5 | — |
| (Flowable of Example 31) | 50 | 90 | | 5 | 5 | 5 | 5 | 5 | 5 | — |
| Composition of the present | 10 | 12.5 | 112.5 | 5 | 5 | 5 | 5 | 5 | 5 | — |
| invention | 20 | 25 | 225 | 5 | 5 | 5 | 5 | 5 | 5 | — |
| (Flowable of Example 32) | 40 | 50 | 450 | 5 | 5 | 5 | 5 | 5 | 5 | — |
| Not treated | | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 27

(field test-3)

| Test agent | Dose of active ingredient g ai/ha | | | Herbicidal effect | | | | | | Phytotoxicity on paddy rice |
|---|---|---|---|---|---|---|---|---|---|---|
| | Component A | Component B | Component B | Hie *1 | Konagi *2 | Azena *3 | Hotarui *4 | Urikawa *5 | Mizugayatsuri *6 | |
| Component A: Compound No. 1 | 15 | | | 4 | 0 | 0 | 0 | 0 | 0 | — |
| (Granule of Comparative | 30 | | | 4 | 1 | 1 | 0 | 0 | 1 | — |
| example 35) | 60 | | | 5 | 2 | 1 | 1 | 2 | 2 | — |
| Component B: NC-311 | | 5 | | 0 | 3 | 4 | 4 | 4 | 3 | — |
| (Granule of Comparative | | 10 | | 1 | 5 | 5 | 4 | 4 | 5 | — |
| example 41) | | 20 | | 2 | 5 | 5 | 5 | 5 | 5 | — |
| Component B: SK-23 | | | 112.5 | 0 | 0 | 0 | 0 | 0 | 0 | — |
| (Granule of Comparative | | | 225 | 0 | 0 | 0 | 1 | 0 | 0 | — |
| example 37) | | | 450 | 0 | 1 | 1 | 2 | 1 | 1 | — |
| Composition of the present | 15 | 5 | | 5 | 5 | 4 | 5 | 5 | 4 | — |
| invention | 30 | 10 | | 5 | 5 | 5 | 5 | 5 | 5 | — |
| (Granule of Example 35) | 60 | 20 | | 5 | 5 | 5 | 5 | 5 | 5 | — |
| Composition of the present | 15 | 5 | 112.5 | 5 | 5 | 5 | 5 | 5 | 5 | — |
| invention | 30 | 10 | 225 | 5 | 5 | 5 | 5 | 5 | 5 | — |
| (Granule of Example 36) | 60 | 20 | 450 | 5 | 5 | 5 | 5 | 5 | 5 | — |
| Component A: Compound No. 1 | 10 | | | 4 | 0 | 0 | 0 | 0 | 0 | — |
| (Flowable of Comparative | 20 | | | 5 | 1 | 0 | 0 | 0 | 0 | — |
| example 38) | 40 | | | 5 | 3 | 1 | 1 | 1 | 2 | — |
| Component B: NC-311 | | 5 | | 0 | 5 | 4 | 4 | 4 | 4 | — |
| (Flowable of Comparative | | 10 | | 1 | 5 | 5 | 4 | 4 | 5 | — |
| example 42) | | 20 | | 2 | 5 | 5 | 5 | 5 | 5 | — |
| Component B: SK-23 | | | 112.5 | 0 | 0 | 0 | 0 | 0 | 0 | — |
| (Flowable of Comparative | | | 225 | 0 | 0 | 0 | 2 | 0 | 0 | — |
| example 40) | | | 450 | 0 | 1 | 1 | 3 | 0 | 1 | — |
| Composition of the present | 10 | 5 | | 5 | 5 | 4 | 5 | 5 | 5 | — |
| invention | 20 | 10 | | 5 | 5 | 5 | 5 | 5 | 5 | — |
| (Flowable of Example 37) | 40 | 20 | | 5 | 5 | 5 | 5 | 5 | 5 | — |
| Composition of the present | 10 | 5 | 112.5 | 5 | 5 | 5 | 5 | 5 | 5 | — |
| invention | 20 | 10 | 225 | 5 | 5 | 5 | 5 | 5 | 5 | — |
| (Flowable of Example 38) | 40 | 20 | 450 | 5 | 5 | 5 | 5 | 5 | 5 | — |
| Not treated | | | | 0 | 0 | 0 | 0 | 0 | 0 | — |

Note:
*1 Hie: *Echinochloa oryzicola* (common name: Early watergrass)
*2 Konagi: Monochoria vaginalis
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

TABLE 28

(field test-4)

| Test agent | Dose of active ingredient g ai/ha | | | | Herbicidal effect | | | | | | Phytotoxicity on paddy rice |
|---|---|---|---|---|---|---|---|---|---|---|---|
| | Component A | Component B | Component B | Component B | Hie *1 | Konagi *2 | Azena *3 | Hotarui *4 | Urikawa *5 | Mizugayatsuri *6 | |
| Component A: Compound No. 1 | 15 | | | | 4 | 0 | 0 | 0 | 0 | 0 | — |
| (Granule of Comparative | 30 | | | | 4 | 1 | 1 | 0 | 0 | 0 | — |
| example 29) | 60 | | | | 5 | 2 | 1 | 1 | 2 | 2 | — |
| Component B: DPX-84 | | 7.5 | | | 0 | 2 | 2 | 3 | 3 | 3 | — |
| (Granule of Comparative | | 15 | | | 0 | 3 | 3 | 3 | 3 | 3 | — |
| example 43) | | 30 | | | 1 | 4 | 5 | 4 | 4 | 4 | — |
| Component B: DPX-47 | | | 1.5 | | 0 | 2 | 2 | 3 | 3 | 4 | — |
| (Granule of Comparative | | | 3 | | 0 | 3 | 3 | 4 | 4 | 5 | — |
| example 44) | | | 6 | | 1 | 3 | 3 | 4 | 5 | 5 | — |
| Component B: SK-23 | | | | 113 | 0 | 0 | 0 | 0 | 0 | 0 | — |
| (Granule of Comparative | | | | 225 | 0 | 0 | 0 | 1 | 0 | 0 | — |
| example 45) | | | | 450 | 0 | 1 | 1 | 2 | 1 | 1 | — |

TABLE 28-continued (field test-4)

| Test agent | Dose of active ingredient g ai/ha | | | | Herbicidal effect | | | | | | Phytotoxicity on paddy rice |
|---|---|---|---|---|---|---|---|---|---|---|---|
| | Component A | Component B | Component B | Component B | Hie *1 | Konagi *2 | Azena *3 | Hotarui *4 | Urikawa *5 | Mizugayatsuri *6 | |
| Composition of the present | 15 | 7.5 | 1.5 | | 5 | 5 | 3 | 3 | 4 | 4 | — |
| invention | 30 | 15 | 3 | | 5 | 5 | 5 | 5 | 5 | 5 | — |
| (Granule of Example 41) | 60 | 30 | 6 | | 5 | 5 | 5 | 5 | 5 | 5 | — |
| Composition of the present | 15 | 7.5 | 1.5 | 113 | 5 | 5 | 5 | 5 | 5 | 5 | — |
| invention | 30 | 15 | 3 | 225 | 5 | 5 | 5 | 5 | 5 | 5 | — |
| (Granule of Example 42) | 60 | 30 | 6 | 450 | 5 | 5 | 5 | 5 | 5 | 5 | — |
| Component A: Compound No. 1 | 10 | | | | 4 | 0 | 0 | 0 | 0 | 0 | — |
| (Flowable of Comparative | 20 | | | | 5 | 1 | 0 | 0 | 0 | 0 | — |
| example 46) | 40 | | | | 5 | 3 | 1 | 1 | 1 | 2 | — |
| Component B: DPX-84 | | 7.5 | | | 0 | 2 | 2 | 2 | 3 | 3 | — |
| (Flowable of Comparative | | 15 | | | 0 | 3 | 4 | 3 | 3 | 3 | — |
| example 47) | | 30 | | | 1 | 4 | 5 | 4 | 4 | 4 | — |
| Component B: DPX-47 | | | 1.5 | | 0 | 2 | 2 | 3 | 4 | 4 | — |
| (Flowable of Comparative | | | 3 | | 0 | 3 | 2 | 4 | 4 | 5 | — |
| example 48) | | | 6 | | 1 | 3 | 3 | 5 | 5 | 5 | — |
| Component B: SK-23 | | | | 113 | 0 | 0 | 0 | 0 | 0 | 0 | — |
| (Flowable of Comparative | | | | 225 | 0 | 0 | 0 | 2 | 0 | 0 | — |
| example 49) | | | | 450 | 0 | 1 | 1 | 3 | 0 | 1 | — |
| Composition of the present | 10 | 7.5 | 1.5 | | 5 | 5 | 4 | 3 | 5 | 4 | — |
| invention | 20 | 15 | 3 | | 5 | 5 | 5 | 5 | 5 | 5 | — |
| (Flowable of Example 43) | 40 | 30 | 6 | | 5 | 5 | 5 | 5 | 5 | 5 | — |
| Composition of the present | 10 | 7.5 | 1.5 | 113 | 5 | 5 | 5 | 5 | 5 | 5 | — |
| invention | 20 | 15 | 3 | 225 | 5 | 5 | 5 | 5 | 5 | 5 | — |
| (Flowable of Example 44) | 40 | 30 | 6 | 450 | 5 | 5 | 5 | 5 | 5 | 5 | — |
| Not treated | | | | | 0 | 0 | 0 | 0 | 0 | 0 | — |

Note:
*1 Hie: *Echinochloa oryzicola* (common name: Early watergrass)
*2 Konagi: *Monochoria vaginalis*
*3 Azena: *Lindernia procumbens* (common name: Common falsepimpernel)
*4 Hotarui: *Scirpus juncoides* (common name: Japanese bulrush)
*5 Urikawa: *Sagittaria pygmaea*
*6 Mizugayatsuri: *Cyperus serotinus*

We claim:

1. A herbicidal composition containing as active ingredients the following two components A and B.

Component A:
at least one derivative selected from the 1,3-oxazin-4-one derivatives represented by the following general formula (I)

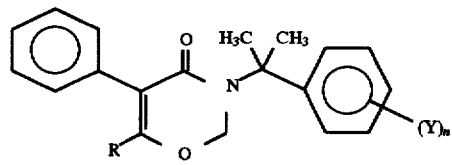

wherein, R is a methyl or an ethyl group, Y is a halogen atom, a lower haloalkyl or a lower haloalkoxy group, and n is 0, 1, 2 or 3, and Component B:
at least one compound selected from
5-tert-butyl-3-(2,4-dichloro-5-isopropoxy-phenyl)-1,3,4-oxadiazol-2-(3H)one,
1,3-dimethyl-4-(2,4-dichloro-3-methylbenzoyl)-5-(4-methyl-phenacyloxy)pyrazole,
2-(2,4-dichloro-m-tolyloxy)propionanilide,
(RS)-2-bromo-3,3-dimethyl-N-(1-methyl-1-phenylethyl)-3,3-dimethylbutylamide,
2,3-dihydro-3,3-dimethylbenzofuran-5-yl ethanesulfonate,
1-(α,α-dimethylbenzyl)-3-p-tolylurea,
1-(2-chlorobenzyl)-3-(α,α-dimethylbenzyl)urea,
4'-nitrophenyl-2,4,6-trichlorophenyl ether, methyl 5-(2,4-dichlorophenoxy)-2-nitrobenzoate,
2,4-bis(ethylamino)-6-methylthio-S-triazine and
2-(1,2-dimethylpropylamino)-4-ethylamino-6-methylthio-1,3,5-triazine,
N'-(2-chloroimidazol[1,2,-a]pyridin-3-yl-sulfonyl)-N'-(4,6-dimethoxy-2-pyrimidyl)urea,
methyl 2-[[[[[(4,6-dimethoxy-2-pyrimidinyl)-amino]carbonyl]amino]sulfonyl]methyl]benzoate,
ethyl 5-(4,6-dimethoxypyrimidin-2-yl-carbamoyl-sulfamoyl)-1-methylpyrazole-4-carboxylate, and
5-[(4,6-dimethoxypyrimidin-2-yl)aminocarbonyl-aminosulfonyl]-1-methyl-4-(2-methyl-1,2,3,4-tetrazol-5-yl)-pyrazole.

2. The herbicidal composition according to claim 1 wherein said component A is 6-methyl-3-[1-methyl-1-(3,5-dichlorophenyl)ethyl]-5-phenyl-2,3-dihydro-4H-1,3-oxazin-4-one.

3. The herbicidal composition according to claim 1 wherein said component A is 6-methyl-3-[1-methyl-1-(3,5-dichlorophenyl)ethyl]-5-phenyl-2,3-dihydro-4H-1,3- oxazin-4-one, and said component B is t-tert butyl-3-(2,4-di-chloro-5-isopropoxyphenyl)-1,3,4-oxadiazol-2-(3H)-one.

4. The herbicidal composition according to claim 1 wherein said component A is 6-methyl-3-[1-methyl-1-(3,5-dichlorophenyl)ethyl]-5-phenyl-2,3-dihydro-4H-1,3-oxazin-4-one, and said component B is 1,3-dimethyl-4-(2,4-di-chloro-3-methylbenzoyl)-5-(4-methyl-phenacyloxy) pyrazole.

5. The herbicidal composition according to claim 1 wherein said component A is 6-methyl-3-[1-methyl-1-(3,5-dichlorophenyl)ethyl]-5-phenyl-2,3-dihydro-4H-1,3-oxazin-4-one, and said component B is 1-(α,α-dimethylbenzyl)-3-p-tolylurea.

6. The herbicidal composition according to claim 1 wherein said component A is 6-methyl-3-[1-methyl-1-(3,5-dichlorophenyl)ethyl]-5-phenyl-2,3-dihydro-4H-1,3-oxazin-4-one, and said component B is 4'-nitrophenyl-2,4,6-trichlorophenyl ether.

7. The herbicidal composition according to claim 1 wherein said component A is 6-methyl-3-[1-methyl-1-(3,5-dichlorophenyl)ethyl]-5-phenyl-2,3-dihydro-4H-1,3-oxazin-4-one, and said component B is methyl 5-(2,4-dichlorophenoxy)-2-nitrobenzoate.

8. The herbicidal composition according to claim 1 wherein said component A is 6-methyl-3-[1-methyl-1-(3,5-dichlorophenyl)ethyl]-5-phenyl-2,3-dihydro-4H-1,3-oxazin-4-one, and said component B are 1,3-dimethyl-4-(2,4-di-chloro-3-methylbenzoyl)-5-(4-methyl-phenacyloxy) pyrazole and 2-bromo-3,3-dimethyl-N-(1-methyl-1-phenylethyl)butyl-amide.

9. The herbicidal composition according to claim 1 wherein said component A is 6-methyl-3-[1-methyl-1-(3,5-dichlorophenyl)ethyl]-5-phenyl-2,3-dihydro-4H-1,3-oxazin-4-one, and said component B are 1,3-dimethyl-4-(2,4-di-chloro-3-methylbenzoyl)-5-(4-methyl-phenacyloxy) pyrazole and 1-(2-chlorobenzyl)-3-(α,α-dimethylbenzyl) urea.

10. The herbicidal composition according to claim 1 wherein said component A is 6-methyl-3-[1-methyl-1-(3,5-dichlorophenyl)ethyl]-5-phenyl-2,3-dihydro-4H-1,3-oxazin-4-one, and said component B is 1,3-dimethyl-4-(2,4-dichloro-3-methylbenzoyl)-5-(4-methyl-phenacyloxy) pyrazole, 2-(2,4-dichloro-m-tolyloxy)propionanilide and (RS)-2-bromo-3,3-dimethyl-N-(1-methyl-1-phenylethyl)-3,3- dimethylbutylamide.

11. The herbicidal composition according to claim 1 wherein said component A is 6-methyl-3-[1-methyl-1-(3,5-dichlorophenyl)ethyl]-5-phenyl-2,3-dihydro-4H-1,3-oxazin-4-one, and said component B are 1,3-dimethyl-4-(2,4-di-chloro-3-methylbenzoyl)-5-(4-methyl-phenacyloxy) pyrazole, 2-(2,4-dichloro-m-tolyloxy)propionanilide and 2,3-dihydro-3,3-dimethylbenzofuran-5-yl ethanesulfonate.

12. The herbicidal composition according to claim 1 wherein said component A is 6-methyl-3-[1-methyl-1-(3,5-dichlorophenyl)ethyl]-5-phenyl-2,3-dihydro-4H-1,3-oxazin-4-one, and said component B is 2,4-bis(ethylamino)-6-methylthio- 3-triazine.

13. The herbicidal composition according to claim 1 wherein said component A is 6-methyl-3-[1-methyl-1-(3,5-dichlorophenyl)ethyl]-5-phenyl-2,3-dihydro-4H-1,3-oxazin-4-one, and said component B is N'-(2-chloroimidazol[1,2,-a]pyridin-3-yl-sulfonyl)-N'-(4,6-dimethoxy-2-pyrimidyl)-urea.

14. The herbicidal composition according to claim 1 wherein said component A is 6-methyl-3-[1-methyl-1-(3,5-dichlorophenyl)ethyl]-5-phenyl-2,3-dihydro-4H-1,3-oxazin-4-one, and said component B are N'-(2-chloroimidazol[1,2,-a]pyridin-3-yl-sulfonyl)-N'-(4,6-dimethoxy-2-pyrimidyl)-urea and 1-(α,α-dimethylbenzyl)-3-p-tolylurea.

15. The herbicidal composition according to claim 1 wherein said component A is 6-methyl-3-[1-methyl-1-(3,5-dichlorophenyl)ethyl]-5-phenyl-2,3-dihydro-4H-1,3-oxazin-4-one, and said component B is methyl 2-[[[[(4,6-di-methoxy-2-pyrimidinyl)amino]carbonyl]amino]sulfonyl]-methyl]benzoate.

16. The herbicidal composition according to claim 1 wherein said component A is 6-methyl-3-[1-methyl-1-(3,5-dichlorophenyl)ethyl]-5-phenyl-2,3-dihydro-4H-1,3-oxazin-4-one, and said component B are methyl 2-[[[[(4,6-di-methoxy-2-pyrimidinyl)amino]carbonyl]amino]sulfonyl]-methyl]benzoate and 1-(α,α-dimethylbenzyl)-3-p-tolylurea.

17. The herbicidal composition according to claim 1 wherein said component A is 6-methyl-3-[1-methyl-1-(3,5-dichlorophenyl)ethyl]-5-phenyl-2,3-dihydro-4H-1,3-oxazin-4-one, and said component B is ethyl 5-(4,6-dimethoxy-pyrimidin-2-yl-carbamoylsulfamoyl)-1-methylpyrazole-4-carboxylate.

18. The herbicidal composition according to claim 1 wherein said component A is 6-methyl-3-[1-methyl-1-(3,5-dichlorophenyl)ethyl]-5-phenyl-2,3-dihydro-4H-1,3-oxazin-4-one, and said component B are ethyl 5-(4,6-dimethoxy-pyrimidin-2-yl-carbamoylsulfamoyl)-1-methylpyrazole-4-carboxylate and 1-(α,α-dimethylbenzyl)-3-p-tolylurea.

19. The herbicidal composition according to claim 1 wherein said component A is 6-methyl-3-[1-methyl-1-(3,5-dichlorophenyl)ethyl]-5-phenyl-2,3-dihydro-4H-1,3-oxazin-4-one, and said component B are methyl 2-[[[[(4,6-di-methoxy-2-pyrimidinyl)amino]carbonyl]amino]sulfonyl]-methyl]benzoate and 5-[(4,6-dimethoxypyrimidin-2-yl)-aminocarbonylaminosulfonyl]-1-methyl-4-(2-methyl-1,2,3,4-tetrazol-5-yl)-pyrazole.

20. The herbicidal composition according to claim 1 wherein said component A is 6-methyl-3-[1-methyl-1-(3,5-dichlorophenyl)ethyl]-5-phenyl-2,3-dihydro-4H-1,3-oxazin-4-one, and said component B are methyl 2-[[[[(4,6-di-methoxy-2-pyrimidinyl)amino]carbonyl]amino]sulfonyl]-methyl]benzoate and 5-[(4,6-dimethoxypyrimidin-2-yl)-aminocarbonylaminosulfonyl]-1-methyl-4-(2-methyl-1,2,3,4-tetrazol-5-yl)-pyrazole and 1-(α,α-dimethyl-benzyl)-3-p-tolylurea.

21. The herbicidal composition according to claim 1 which contains said component B in an amount of 0.01 to 1,000 weight parts, preferably 0.1 to 500 weight parts per weight of said component A.

22. The herbicidal composition according to claim 1 which is in the form of a granule, a wettable powder or a flowable formulate.

23. A process for preparing a herbicidal composition characterized by formulating said component A and said component B disclosed in claim 1, together with auxiliaries for formulation which are acceptable in agriculture or horticulture, into a form usually used in pesticides.

* * * * *